(12) United States Patent
Opolski et al.

(10) Patent No.: US 9,084,603 B2
(45) Date of Patent: Jul. 21, 2015

(54) CATCH MEMBERS FOR OCCLUDER DEVICES

(71) Applicant: W.L. Gore & Associates, Inc., Flagstaff, AZ (US)

(72) Inventors: Steven W. Opolski, Carlisle, MA (US); Sean T. Forde, Watertown, MA (US); Stephanie M. Kladakis, Watertown, MA (US); David J. Callaghan, Boston, MA (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

(21) Appl. No.: 14/078,330

(22) Filed: Nov. 12, 2013

(65) Prior Publication Data
US 2014/0222058 A1    Aug. 7, 2014

Related U.S. Application Data

(62) Division of application No. 11/644,373, filed on Dec. 21, 2006, now abandoned.

(60) Provisional application No. 60/753,681, filed on Dec. 22, 2005.

(51) Int. Cl.
*A61B 17/08* (2006.01)
*A61B 17/12* (2006.01)
*A61B 17/00* (2006.01)

(52) U.S. Cl.
CPC ......... *A61B 17/1215* (2013.01); *A61B 17/0057* (2013.01); *A61B 2017/00004* (2013.01);
(Continued)

(58) Field of Classification Search
CPC ............... A61B 17/0057; A61B 2017/00619; A61B 2017/00575; A61B 2017/00606; A61B 2017/00623
USPC ................ 606/151, 157, 158, 200, 213, 215; 604/104–108
See application file for complete search history.

(56) References Cited

U.S. PATENT DOCUMENTS

| | | | |
|---|---|---|---|
| 3,874,388 A | 4/1975 | King et al. | |
| 3,875,648 A | 4/1975 | Bone | |

(Continued)

FOREIGN PATENT DOCUMENTS

| | | |
|---|---|---|
| DE | 9413645 U1 | 10/1994 |
| EP | 0362113 | 4/1990 |

(Continued)

OTHER PUBLICATIONS

U.S. Appl. No. 60/662,990.
(Continued)

*Primary Examiner* — Alexander Orkin
(74) *Attorney, Agent, or Firm* — DLA Piper LLP (US)

(57) ABSTRACT

Devices and techniques for modifying and maintaining a configuration of an occlusion device for the closure of physical anomalies, such as an atrial septal defect, a patent foramen ovale (PFO), and other septal and vascular defects are described. The devices and techniques relate particularly to, but are not limited to, modifying and maintaining a configuration of a PFO occluder made from a polymer tube. The proximal portion of a catch member may be provided with one or more protrusions, or arms, or bump or other raised element for securing the occluder in a partial or fully deployed configuration, either temporarily or permanently.

2 Claims, 19 Drawing Sheets

(52) U.S. Cl.
CPC ............... *A61B2017/00575* (2013.01); *A61B 2017/00592* (2013.01); *A61B 2017/00606* (2013.01); *A61B 2017/00619* (2013.01); *A61B 2017/00623* (2013.01)

(56) References Cited

U.S. PATENT DOCUMENTS

| | | | |
|---|---|---|---|
| 3,924,631 A | 12/1975 | Mancusi, Jr. |
| 4,006,747 A | 2/1977 | Kronenthal et al. |
| 4,007,743 A | 2/1977 | Blake |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behi |
| 5,108,420 A | 4/1992 | Marks |
| 5,149,327 A | 9/1992 | Oshiyama et al. |
| 5,152,144 A | 10/1992 | Andrie et al. |
| 5,167,637 A | 12/1992 | Okada et al. |
| 5,171,259 A | 12/1992 | Inoue et al. |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,334,217 A | 8/1994 | Das |
| 5,350,363 A | 9/1994 | Goode et al. |
| 5,354,308 A | 10/1994 | Simon et al. |
| 5,411,481 A | 5/1995 | Allen et al. |
| 5,413,584 A | 5/1995 | Schulze et al. |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,478,353 A | 12/1995 | Yoon |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt et al. |
| 5,709,707 A | 1/1998 | Lock et al. |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,957,953 A | 9/1999 | DiPoto et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassily et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt et al. |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |

(56) References Cited

U.S. PATENT DOCUMENTS

| | | | |
|---|---|---|---|
| 6,344,048 B1 | 2/2002 | Chin et al. | |
| 6,344,049 B1 | 2/2002 | Levinson et al. | |
| 6,346,074 B1 | 2/2002 | Roth | |
| 6,348,041 B1 | 2/2002 | Klint et al. | |
| 6,352,552 B1 | 3/2002 | Levinson et al. | |
| 6,355,052 B1 | 3/2002 | Neuss et al. | |
| 6,356,782 B1 | 3/2002 | Sirimanne et al. | |
| 6,364,853 B1 | 4/2002 | French et al. | |
| 6,371,904 B1 | 4/2002 | Sirimanne et al. | |
| 6,375,625 B1 | 4/2002 | French et al. | |
| 6,375,671 B1 | 4/2002 | Kobayashi et al. | |
| 6,379,342 B1 | 4/2002 | Levinson | |
| 6,379,368 B1 | 4/2002 | Corcoran et al. | |
| 6,387,104 B1 | 5/2002 | Pugsley, Jr. et al. | |
| 6,398,796 B2 | 6/2002 | Levinson | |
| 6,402,772 B1 | 6/2002 | Amplatz et al. | |
| 6,419,669 B1 | 7/2002 | Frazier et al. | |
| 6,426,145 B1 | 7/2002 | Moroni | |
| 6,436,088 B2 | 8/2002 | Frazier et al. | |
| 6,440,152 B1 | 8/2002 | Gainor et al. | |
| 6,460,749 B1 | 10/2002 | Levinson et al. | |
| 6,482,224 B1 | 11/2002 | Michler et al. | |
| 6,488,706 B1 | 12/2002 | Solymar et al. | |
| 6,494,888 B1 | 12/2002 | Laufer et al. | |
| 6,508,828 B1 | 1/2003 | Akerfeldt et al. | |
| 6,514,515 B1 | 2/2003 | Williams | |
| 6,548,569 B1 | 4/2003 | Williams et al. | |
| 6,551,303 B1 | 4/2003 | Van Tassel et al. | |
| 6,551,344 B2 | 4/2003 | Thill | |
| 6,585,755 B2 | 7/2003 | Jackson et al. | |
| 6,596,013 B2 | 7/2003 | Yang et al. | |
| 6,599,448 B2 | 7/2003 | Ehrhard, Jr. et al. | |
| 6,610,764 B1 | 8/2003 | Martin et al. | |
| 6,623,508 B2 | 9/2003 | Shaw et al. | |
| 6,623,518 B2 | 9/2003 | Thompson et al. | |
| 6,626,936 B2 | 9/2003 | Stinson | |
| 6,629,901 B2 | 10/2003 | Huang | |
| 6,666,861 B1 | 12/2003 | Grabek | |
| 6,669,722 B2 | 12/2003 | Chen et al. | |
| 6,689,589 B2 | 2/2004 | Huisman et al. | |
| 6,712,804 B2 | 3/2004 | Roue et al. | |
| 6,712,836 B1 | 3/2004 | Berg et al. | |
| 6,726,696 B1 | 4/2004 | Houser et al. | |
| 6,828,357 B1 | 12/2004 | Martin et al. | |
| 6,838,493 B2 | 1/2005 | Williams et al. | |
| 6,867,247 B2 | 3/2005 | Williams et al. | |
| 6,867,248 B1 | 3/2005 | Martin et al. | |
| 6,921,410 B2 | 7/2005 | Porter | |
| 7,198,631 B2 | 4/2007 | Kanner et al. | |
| 2001/0000799 A1* | 5/2001 | Wessman et al. | 606/200 |
| 2001/0014800 A1 | 8/2001 | Frazier et al. | |
| 2001/0034537 A1 | 10/2001 | Shaw et al. | |
| 2001/0034567 A1 | 10/2001 | Allen et al. | |
| 2001/0037129 A1 | 11/2001 | Thill | |
| 2001/0039435 A1 | 11/2001 | Roue et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | |
| 2002/0010481 A1 | 1/2002 | Jayaraman | |
| 2002/0019648 A1 | 2/2002 | Akerfeldt et al. | |
| 2002/0026208 A1 | 2/2002 | Roe et al. | |
| 2002/0029048 A1 | 3/2002 | Miller | |
| 2002/0032459 A1 | 3/2002 | Horzewski et al. | |
| 2002/0032462 A1 | 3/2002 | Houser et al. | |
| 2002/0035374 A1 | 3/2002 | Borillo et al. | |
| 2002/0043307 A1 | 4/2002 | Ishida et al. | |
| 2002/0052572 A1 | 5/2002 | Franco et al. | |
| 2002/0058989 A1 | 5/2002 | Chen et al. | |
| 2002/0077555 A1 | 6/2002 | Schwartz | |
| 2002/0096183 A1 | 7/2002 | Stevens et al. | |
| 2002/0099389 A1 | 7/2002 | Michler et al. | |
| 2002/0107531 A1 | 8/2002 | Schreck et al. | |
| 2002/0111637 A1 | 8/2002 | Kaplan et al. | |
| 2002/0111647 A1 | 8/2002 | Khairkhahan et al. | |
| 2002/0120323 A1 | 8/2002 | Thompson et al. | |
| 2002/0128680 A1 | 9/2002 | Pavlovic | |
| 2002/0129819 A1 | 9/2002 | Feldman et al. | |
| 2002/0164729 A1 | 11/2002 | Skraly et al. | |
| 2002/0169377 A1 | 11/2002 | Khairkhahan et al. | |
| 2002/0183786 A1 | 12/2002 | Girton | |
| 2002/0183787 A1 | 12/2002 | Wahr et al. | |
| 2002/0183823 A1 | 12/2002 | Pappu | |
| 2002/0198563 A1 | 12/2002 | Gainor et al. | |
| 2003/0004533 A1 | 1/2003 | Dieck et al. | |
| 2003/0028213 A1 | 2/2003 | Thill et al. | |
| 2003/0045893 A1 | 3/2003 | Ginn | |
| 2003/0050665 A1 | 3/2003 | Ginn | |
| 2003/0055455 A1 | 3/2003 | Yang et al. | |
| 2003/0059640 A1 | 3/2003 | Marton et al. | |
| 2003/0065379 A1 | 4/2003 | Babbs et al. | |
| 2003/0100920 A1 | 5/2003 | Akin et al. | |
| 2003/1389819 | 7/2003 | Beer et al. | |
| 2003/0150821 A1 | 8/2003 | Bates et al. | |
| 2003/0171774 A1 | 9/2003 | Freudenthal et al. | |
| 2003/0191495 A1 | 10/2003 | Ryan et al. | |
| 2003/0195530 A1 | 10/2003 | Thill | |
| 2003/0204203 A1 | 10/2003 | Khairkhahan et al. | |
| 2004/0044361 A1 | 3/2004 | Frazier et al. | |
| 2004/0073242 A1 | 4/2004 | Chanduszko | |
| 2004/0167566 A1* | 8/2004 | Beulke et al. | 606/200 |
| 2004/0210301 A1 | 10/2004 | Obermiller | |
| 2004/0234567 A1 | 11/2004 | Dawson | |
| 2005/0025809 A1 | 2/2005 | Hasirci et al. | |
| 2005/0043759 A1 | 2/2005 | Chanduszko | |
| 2005/0267523 A1 | 12/2005 | Devellian et al. | |
| 2005/0273135 A1* | 12/2005 | Chanduszko et al. | 606/213 |
| 2006/0122647 A1 | 6/2006 | Callaghan et al. | |
| 2006/0206146 A1* | 9/2006 | Tenerz | 606/213 |
| 2006/0265004 A1 | 11/2006 | Callaghan et al. | |
| 2007/0010851 A1 | 1/2007 | Chanduszko et al. | |

FOREIGN PATENT DOCUMENTS

| | | |
|---|---|---|
| EP | 0474887 A1 | 3/1992 |
| EP | 0839549 A1 | 5/1998 |
| EP | 1013227 A2 | 6/2000 |
| EP | 1046375 A1 | 10/2000 |
| EP | 1222897 A2 | 7/2002 |
| WO | WO-96/25179 A1 | 8/1996 |
| WO | WO-96/31157 A1 | 10/1996 |
| WO | WO-98/07375 A1 | 2/1998 |
| WO | WO-98/08462 | 3/1998 |
| WO | WO-98/16174 | 4/1998 |
| WO | WO-98/29026 A2 | 7/1998 |
| WO | WO-98/51812 | 11/1998 |
| WO | WO-99/05977 A1 | 2/1999 |
| WO | WO-98/18864 | 4/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 A1 | 6/1999 |
| WO | WO 00/27292 A1 | 5/2000 |
| WO | WO-00/44428 A2 | 8/2000 |
| WO | WO-01/21247 A1 | 3/2001 |
| WO | WO-01/30268 A1 | 5/2001 |
| WO | WO-01/49185 A1 | 7/2001 |
| WO | WO-01/78596 A1 | 10/2001 |
| WO | WO-02/17809 A1 | 3/2002 |
| WO | WO-02/24106 A3 | 3/2002 |
| WO | WO-03/024337 A1 | 3/2003 |
| WO | WO-03/053493 A2 | 7/2003 |
| WO | WO-03/059152 | 7/2003 |
| WO | WO-03/077733 A2 | 9/2003 |
| WO | WO-03/082076 | 10/2003 |
| WO | WO-03/103476 A2 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |

(56) References Cited

FOREIGN PATENT DOCUMENTS

| WO | WO-2005/027752 | 3/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

Athanasion, T., "Coronary Artery Bypass with the Use of a Magnetic Distal Anastomotic Device: Surgical Technique and Preliminary Experience." The Heart Surgery Forum #20041024, 2004, 4 pgs.

Bachthaler, M. et al., "Corrosion of Tungsten Coils After Peripheral Vascular Embolization Theraphy: Influence on Outcome and Tungsten Load", *Catherization and Cardiovascular Interventions*, vol, 62, pp. 380-384, 2004.

Davis, R.W., "Invention Disclosure: Mechanism for Providing and Making a Bioresorbable Device Radiopaque", *NMT Medical, Inc.*, 6 pages, 2004.

Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.

Filsoufi, F., et al., "Automated Distal Coronary Bypass with a Novel Magnetic Coupler (MVP system)," J. Thoracic and Cardiovascular Surgery, vol. 127(1), pp. 185-192.

GruPwort zur gemeinsamen Jahrestagung der Oster-reichischen, Deutschen and Schweizerischen Gesellschaft fur Biomedizinische Technik, Sep. 24-27, 2003, St. Virgil/Salzburg.

International International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17390, mailed Oct. 6, 2003 (4 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report; International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US06/009978, mailed Jul. 13, 2006 (2 pgs).

International Search Report, International Application No. PCT/US2006/009978, mailed Jul. 13, 2006 (2 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.

Kimura, A., et al., "Effects of Neutron Irradiation on the Transformation Behavior in Ti—Ni Alloys," Abstract, Proceedings of the Inn Conf. on Mariensitic Transformations, 1992, pp. 935-940.

Klima, U., "Magnetic Vascular Port in Minimally Invasive Direct Coronary Artery Bypass Grafting," Circulation; 2004, 11-55-11-60.

Meditec, Ihre Datenbank fur medizinisch-technisches Wissen, Fiz Technik.

Meier, MD, Bernhard et al., "Contemporary Management of Patent Foramen Ovale," American Heart Association, Inc., Circulation, 2003, vol. 107, pp. 5-9.

Nat'l Aeronautics and Space Administration, "55-Nitinol—The Alloy with a Memory: Its Physical Metallurgy, Properties and Applications," NASA Report, pp. 24-25.

Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No, 1, pp. 14-21, 2000.

Ramanathan, G., et al., "Experimental and Computational Methods for Shape Memory Alloys," 15th ASCE Engineering Mechanics Conference, Jun. 2-5, 2002.

Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.

Ruiz, et al, "The Puncture Technique: A New Method for Transcatheter Closure of Patent Foramen Ovale," Catheterization and Cardiovascular Interventions, 2001, vol. 53, pp, 369-372.

Shabalovskaya, S., "Surface, Corrosion amd Biocompatibility Aspects of Nitinol as and Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stein, H., "Telemanipulator-gestazte Applikation eines magnetischen Gef513-Kopplers am schlagenden Herzen mit dem da Vinci—Surgical-System," Biomedizinische Technik; 2003, vol. 48(9), pp. 230-234.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

* cited by examiner

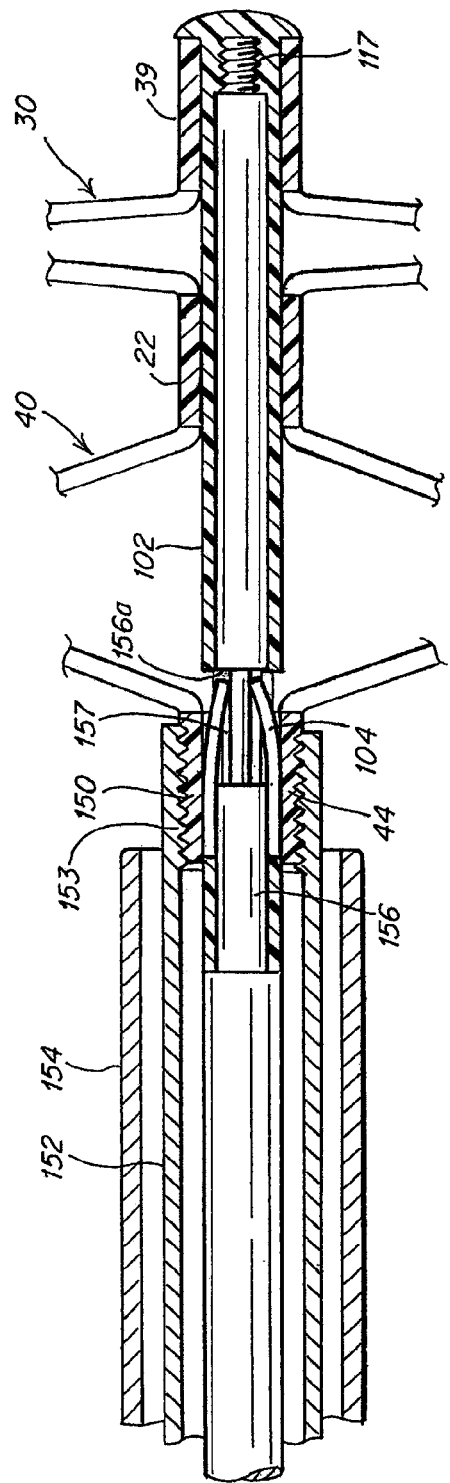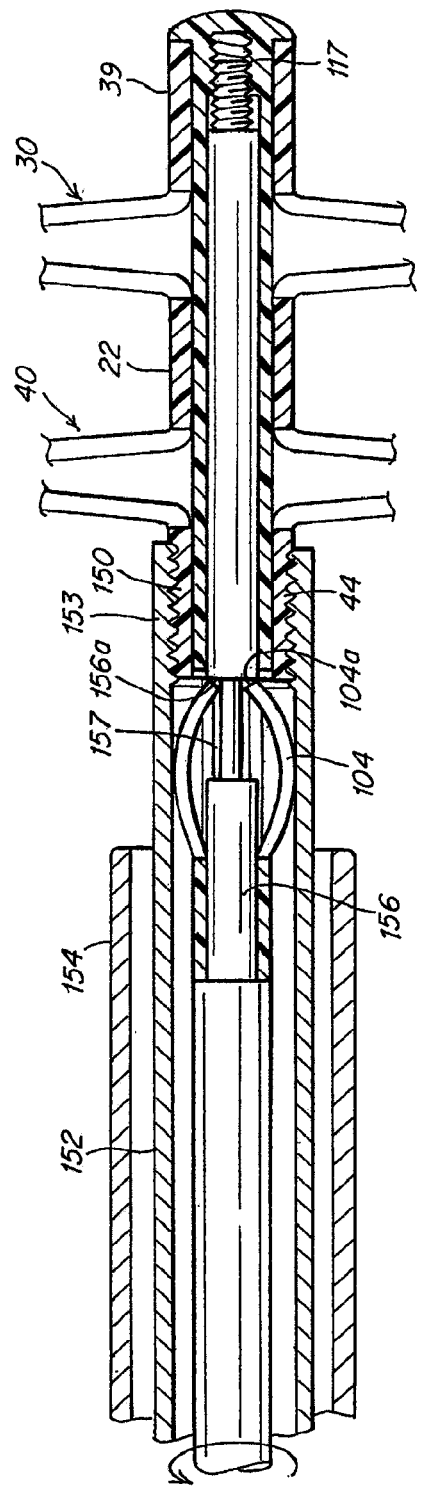

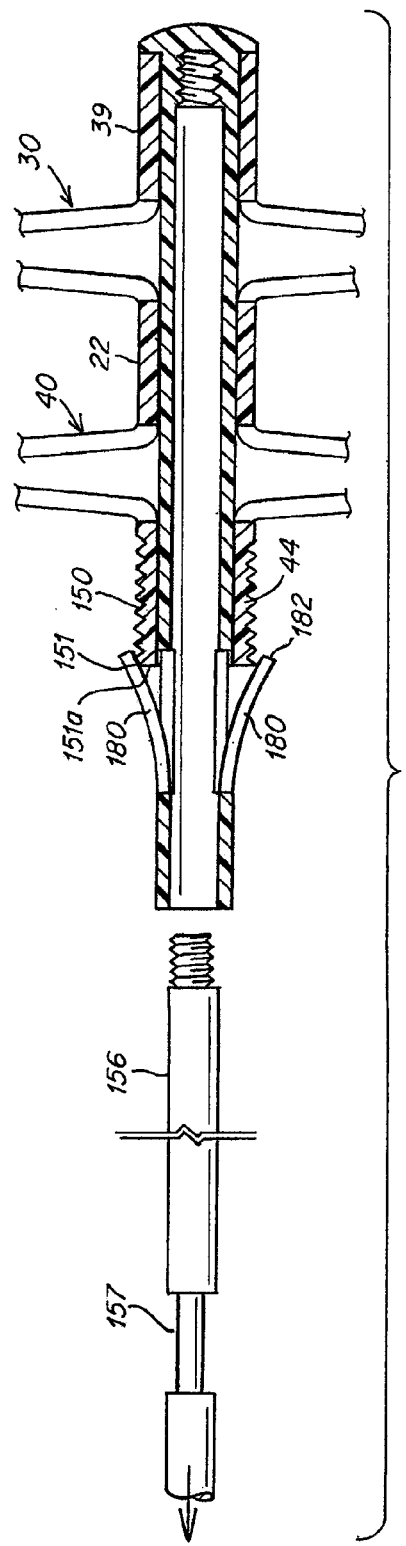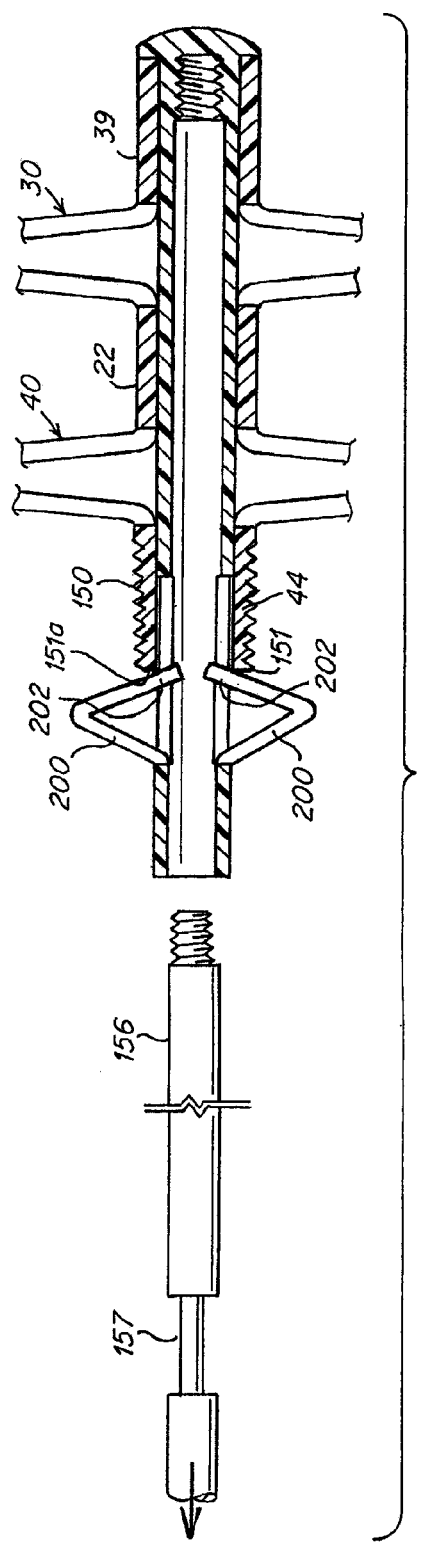

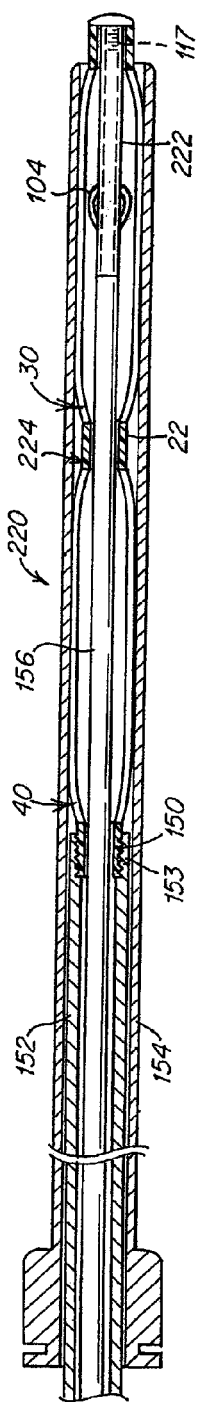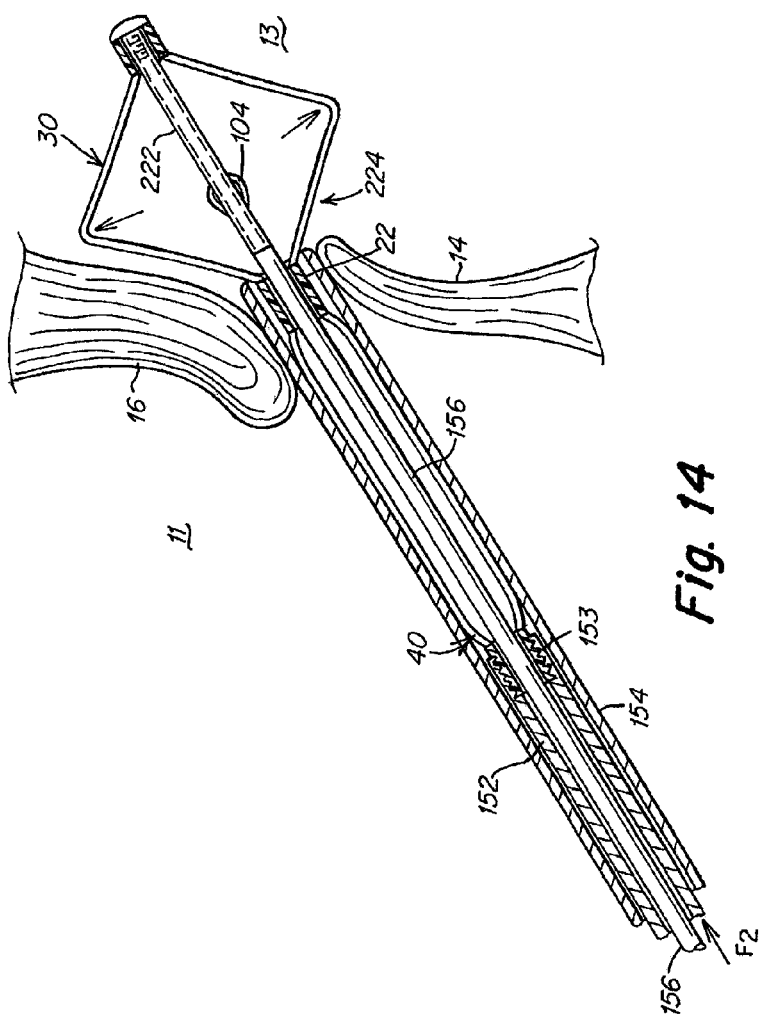
Fig. 13
Fig. 14

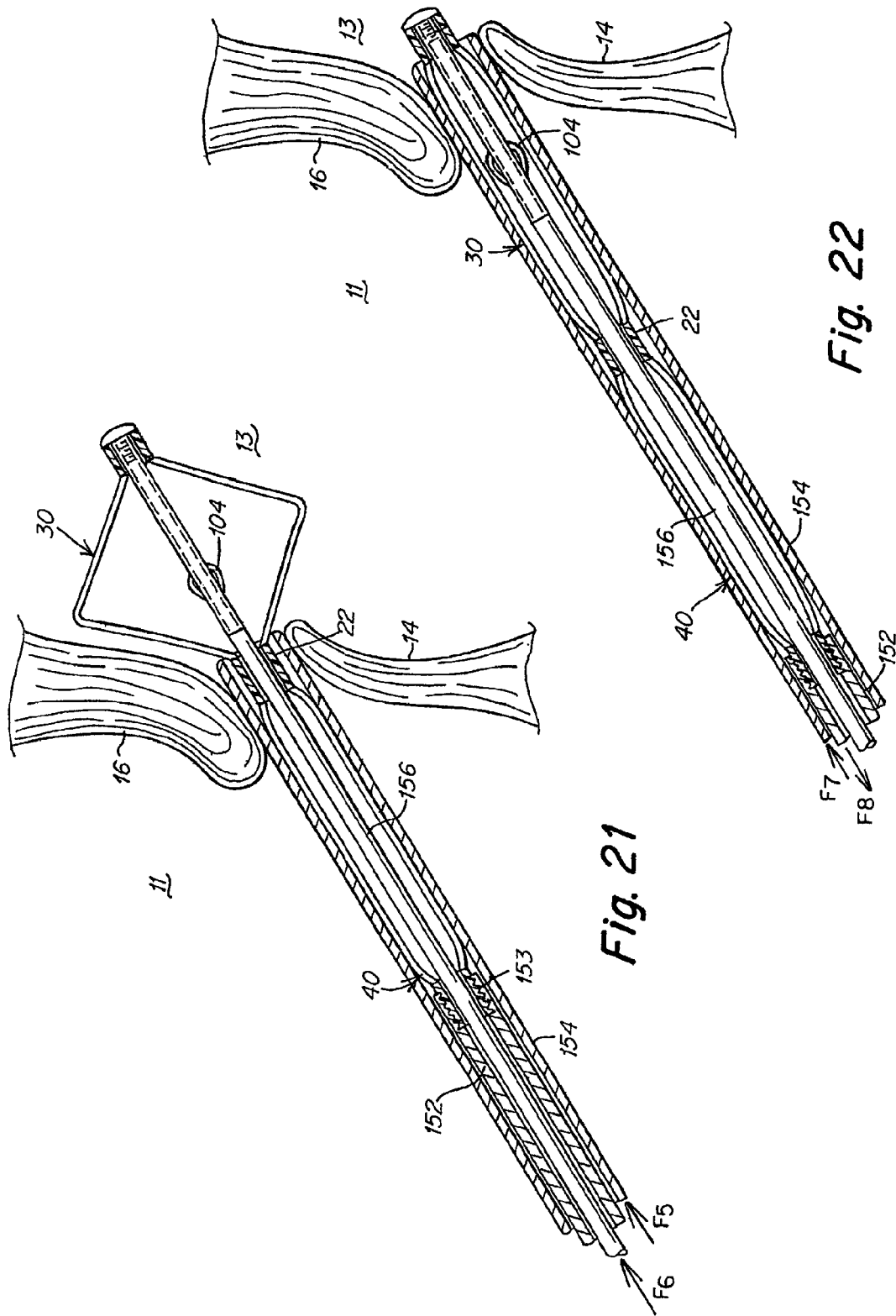

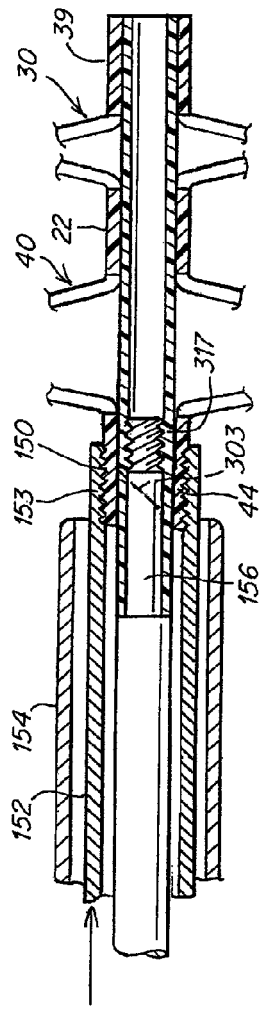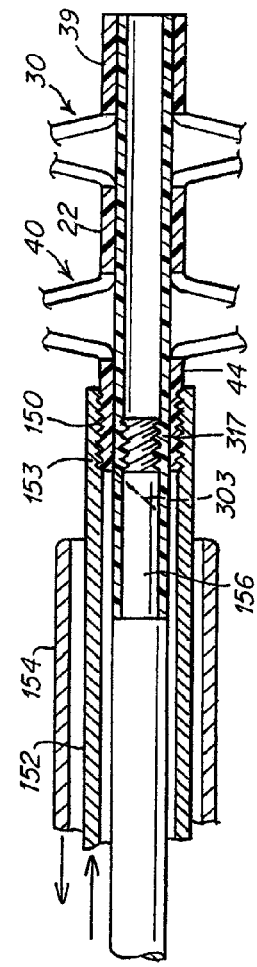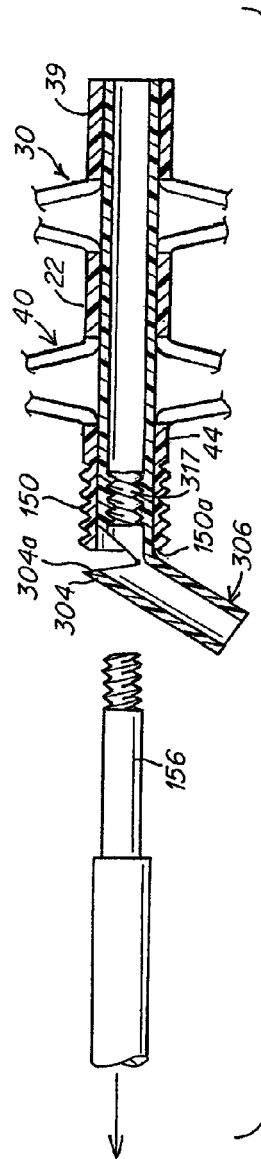

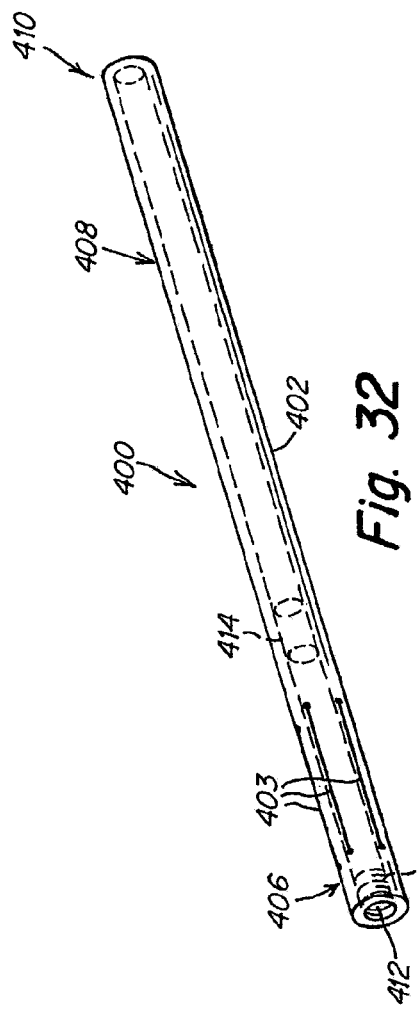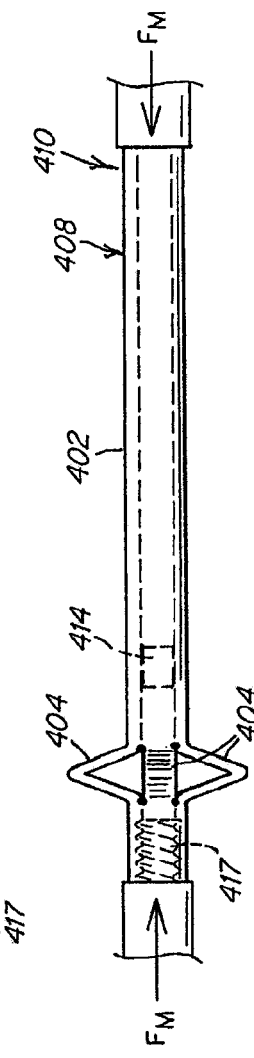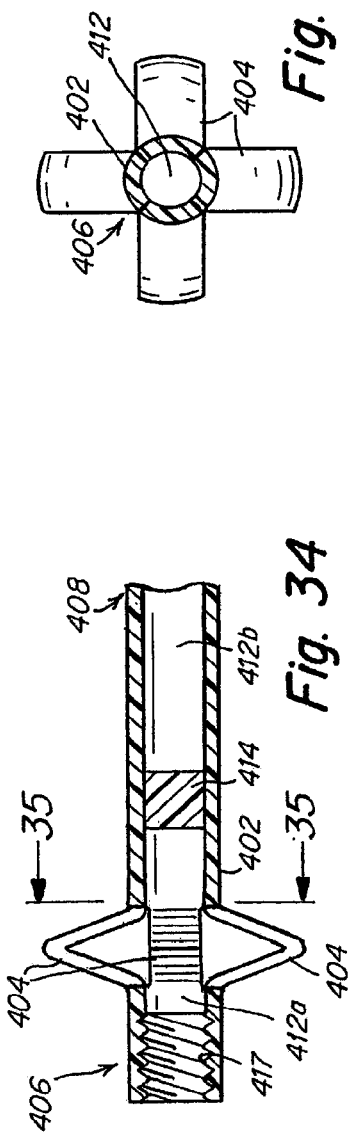

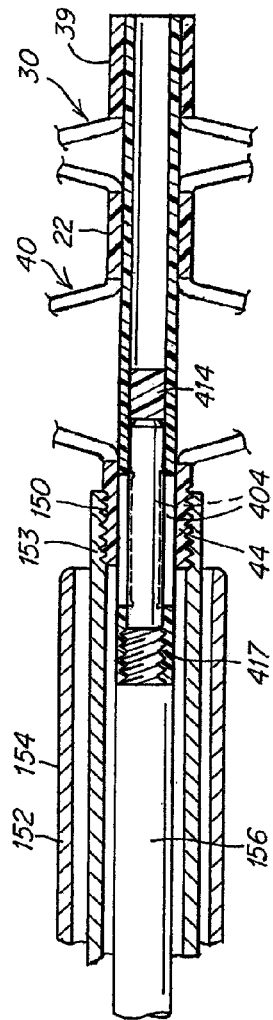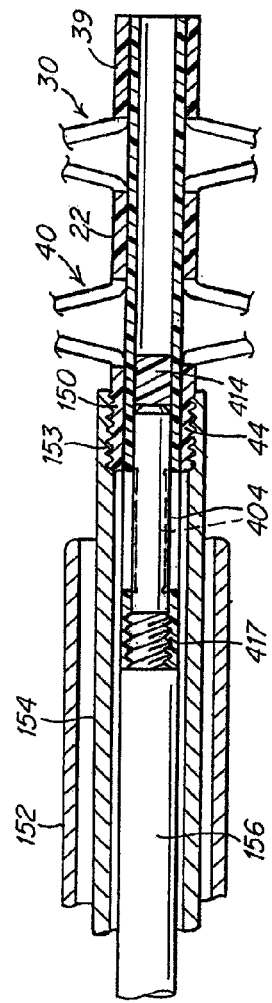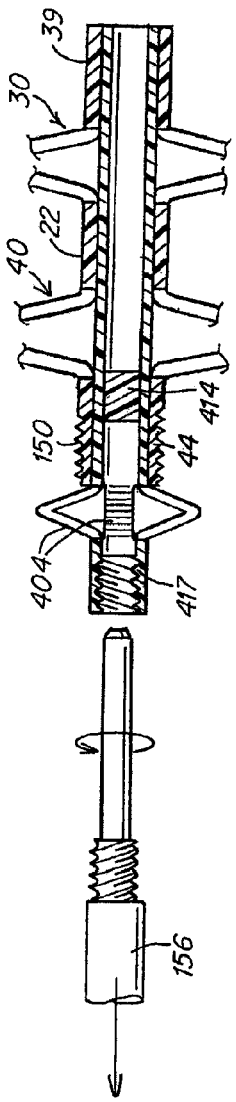

CATCH MEMBERS FOR OCCLUDER DEVICES

CROSS-REFERENCE TO RELATED APPLICATIONS

This application claims the benefit of priority to U.S. Provisional Application Ser. No. 60/753,681, filed Dec. 22, 2005, the disclosure of which is incorporated by reference herein.

FIELD OF THE INVENTION

This invention relates generally to occlusion devices for the closure of physical anomalies, such as an atrial septal defect, a patent foramen ovale, and other septal and vascular defects. The invention also relates to mechanisms for deploying such devices and securing them in the deployed position.

BACKGROUND OF THE INVENTION

A patent foramen ovale (PFO), illustrated in FIG. 1, is a persistent, one-way, usually flap-like opening in the wall between the right atrium 11 and left atrium 13 of the heart 10. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 11 to the left atrium 13 and blood clots could enter the systemic circulation. It is desirable that this circumstance be eliminated.

The foramen ovate serves a desired purpose when a fetus is gestating. Because blood is oxygenated through the umbilical cord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TIA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are significant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

Various designs have disclosed septal closure devices made from a tube. These devices generally have a low septal profile in a delivery configuration, and a high septal profile in a deployed configuration. Upon deployment, these devices seal a septal defect. The unique design of these tube-made devices, however, requires an additional catch mechanism to catch the devices in their deployed configurations.

Various catch member designs have been proposed to catch the tube-made septal closure devices in the deployed configuration, temporary and permanently. Making such catch members capable of forming a temporary lock during partial deployment and a more secure permanent lock after full deployment has proved challenging. Some designs are not sufficiently reliable and other designs cannot be manufactured effectively. Finally, some designs, while workable on paper, do not perform satisfactorily in the human body.

The septal closure devices and techniques disclosed herein are designed to address these and other deficiencies of prior art design and techniques for delivering and retrieving such devices.

BRIEF SUMMARY OF THE INVENTION

In some aspects, the present invention includes several delivery devices and techniques for delivering an implant into a desired location within the body. This delivery technique relates particularly to, but is not limited to, a septal occluder made from a polymer tube. These delivery techniques, in addition to use with septal occluders, can be applied to other medical devices, such as other expandable devices constructed to be delivered in a reduced profile configuration to an expanded profile or delivered configuration.

Catch members may be used to deploy and keep the device in place. According to some embodiments, the catch member maintains a reduced axial length of the device when the device is in the deployed configuration. Also, varied constructions could be used to maintain the axial dimension of the device, such as different locking mechanisms. Preferably, the catch member secures both sides of the device in the reduced profile configuration with a single element. Generally, during the delivery stage, the catch member has a smaller diameter at its proximal end compared to the diameter of the proximal end of the occluder. This configuration allows the proximal end of the occluder to slide over the proximal end of the catch member during deployment sequence. This may be achieved by compression of the proximal end of the catch member, by expansion of the proximal end of the occluder, or a combination of both. In a catching configuration, the catch member generally has a greater diameter at its proximal end compared to the diameter of the proximal end of the occluder, which keeps the occluder in its deployed configuration.

In various embodiments, the catching configuration can be temporary or permanent. A temporary catch configuration generally allows for the catch member to release, while a permanent catch configuration generally is not designed for release. Some embodiments have a temporary catch configuration, which allows for confirmation of proper deployment, and a permanent catch configuration, that is engaged when proper deployment is confirmed.

In certain embodiments, a permanent catch configuration can, for example, have a greater diameter at the proximal end of the catch member than a temporary catch configuration. A temporary catch configuration is generally preferred during evaluation and repositioning of a device, such as an occluder, while a permanent catch configuration is generally preferred once the device is deployed.

According to at least some embodiments, the catch member is formed from a tube. According to some embodiments, the tube includes a material selected from the group consisting of metals, shape memory materials, alloys, polymers, bioabsorbable polymers, and combinations thereof. In particular embodiments, the tube includes a shape memory polymer. In particular embodiments, the tube includes nitinol. In some embodiments, the tube is formed by rolling a flat piece of material into a tubular form. According to some embodiments, the catch member is formed by cutting the tube. The catch member is placed in its deployment configuration by fixing the axial length of the device, for example by preventing the proximal end of the device from sliding over the proximal catch element.

In some embodiments, the catch member uses a partially cut tube, with an axis of the proximal portion of the tube at an angle with respect to the axis of the distal side of the tube. A portion of the proximal side of the tube catches the proximal end of the device and keeps it in a deployed position.

In some embodiments, the catch member uses a series of protrusions at its proximal end. Once the protrusions are released, for example by removing the delivery wire, the protrusions project radially outward from the proximal side of the tube and keep the device in its locked position by preventing the proximal end of the device from sliding over the protrusions. In various embodiments, the protrusions are biased towards the proximal or the distal end of the catch member. In some embodiments, they may be twisted relative to the axis of the catch member.

In certain embodiments, the catch member may include a bump and pre-curved tabs at its proximal side. The bump is interrupted by a largely planar lumen slicing through the proximal side of the catch member. The lumen allows compression of the catch member with the delivery wire attached to provide a temporary catch configuration. In some embodiments, after the delivery wire is removed, the tabs automatically slide into the lumen to prevent or reduce compressibility of the catch member, thus providing a permanent catch configuration.

In a further aspect, the catch member may include a delivery wire and a catch tube that is threadedly secured to the delivery wire at two different locations. Each threaded connection has different pitches. Twisting of the delivery wire with respect to the catch tube creates a temporary or permanent catch depending on the selected design criteria. This system is especially adapted to construction with malleable materials. In another aspect, the protrusions can be threaded with different pitches to allow for modulation of the protrusion configuration by twisting the delivery wire.

These and other aspects and embodiments of the disclosure are illustrated and described below.

BRIEF DESCRIPTION OF THE DRAWINGS

In the Drawings:

FIG. 10 is a cross-sectional side view of one step in a deployment sequence according to one embodiment of the invention;

FIG. 11 is a cross-sectional side view of one step in a deployment sequence according to one embodiment of the invention;

FIG. 12A is a cross-sectional side view of a deployed occluder and a catch member according to one embodiment of the invention;

FIG. 12B is a cross-sectional side view of a deployed occluder and a catch member according to one embodiment of the invention;

FIG. 13 is an axial cross-sectional drawing of an occluder and a catch member, in a delivery configuration, according to one embodiment of the invention;

FIGS. 14-17 are cross-sectional side views of various steps in a deployment sequence according to one embodiment of the invention;

FIGS. 18-22 are cross-sectional side views of various steps in a retrieval sequence according to one embodiment of the invention;

FIGS. 29-30 are cross-sectional side views of various steps in the deployment sequence according to one embodiment of the invention;

FIG. 31 is a cross-sectional side view of the delivery system during the detachment process according to one embodiment of the invention;

FIG. 32 is a view of cuts made during manufacture of a catch member according to one embodiment of the invention;

FIG. 33 is a view of a step in the manufacture of a catch member according to one embodiment of the invention;

FIG. 34 is an expanded cross-sectional side view of the catch member according to one embodiment of the invention;

FIG. 35 is an exploded cross-sectional side view of the catch member along lines 35-35 in FIG. 34 according to one embodiment of the invention;

FIGS. 36-37 are cross-sectional side views of various steps in the deployment sequence according to one embodiment of the invention;

FIG. 38 is a cross-sectional side view of the delivery system during the detachment process according to one embodiment of the invention;

DETAILED DESCRIPTION OF THE ILLUSTRATED EMBODIMENTS

Aspects of the present invention provide devices, delivery/retrieval systems and techniques for delivering such devices intended to occlude an aperture within body tissue. In particular, and as described in detail below, the described occluder may be used for closing an ASD, VSD or PFO in the atrial septum of a heart. Although the embodiments are described with reference to an ASD, VSD or PFO, one skilled in the art will recognize that the device and methods of the present invention may be used to treat other anatomical conditions. As such, the invention should not be considered limited in applicability to any particular anatomical condition. In addition, the systems and methods for delivery and retrieval, and for catching a device in a deployed state, that are aspects of the present invention may also be used in connection with other types of devices besides an occluder, in particular, devices having tubular profiles.

Figure 1:
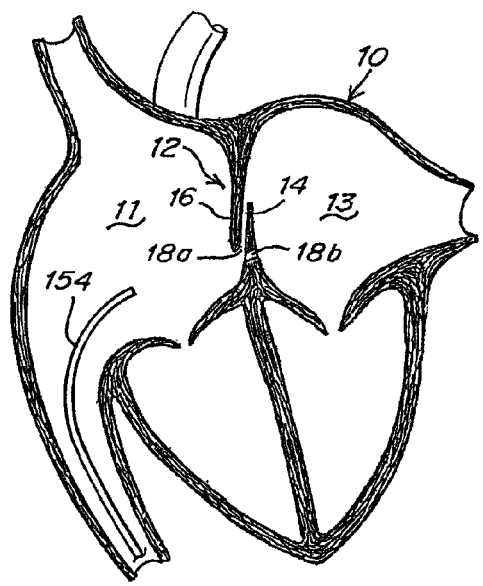
FIG. 1 is a schematic representation of a human heart including various septal defects.
Figure 2:
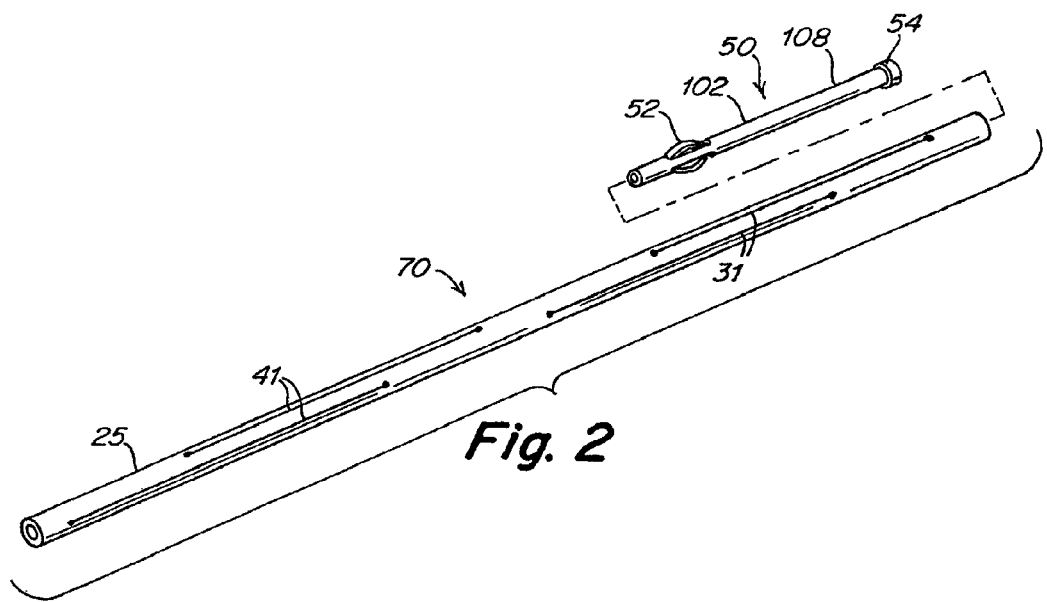
FIG. 2 shows an occluder and a catch member according to one embodiment of the disclosure.

FIG. 1 illustrates a human heart 10, having a right atrium 11 and a left atrium 13 and including various anatomical apertures 18a and 18b. The atrial septum 12 includes septum primum 14 and septum secundum 16. The anatomy of the septum 12 varies widely within the population. In some people, septum primum 14 extends to and overlaps with septum secundum 16. The septum primum 14 may be quite thin. When the anatomical apertures 18a is present, blood could travel through the anatomical aperture 18a between septum primum 14 and septum secundum 16 (referred to as "the PFO tunnel"). Additionally, or alternatively, the presence of an ASD could permit blood to travel through an aperture in the septal tissue, such as through the anatomical aperture 18b.

In this application, "distal" refers to the direction away from a catheter insertion location and "proximal" refers to the direction nearer the insertion location. Additionally, the term "delivery configuration" refers to the configuration of a device, such as an occluder, when it has a reduced profile in a delivery sheath or catheter. The term "deployed configuration" refers to the configuration of the device, such as an occluder, when it has deployed from the catheter, such as at the desired implantation location.

Figure 3:
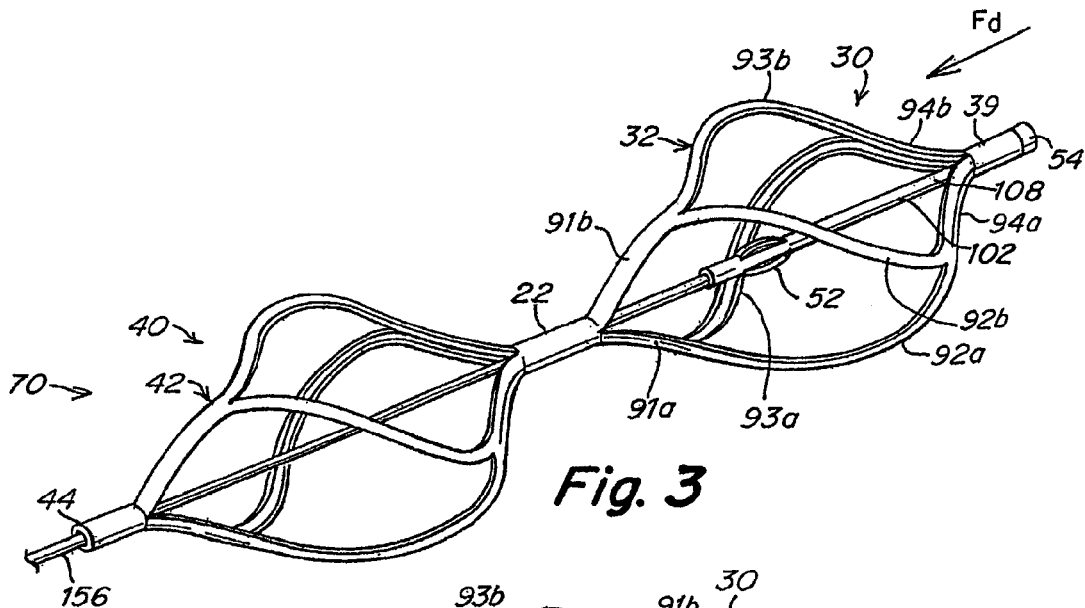
FIG. 3 illustrates an occluder and a catch member during the initial stage of deployment according to one embodiment of the invention.
Figure 4:
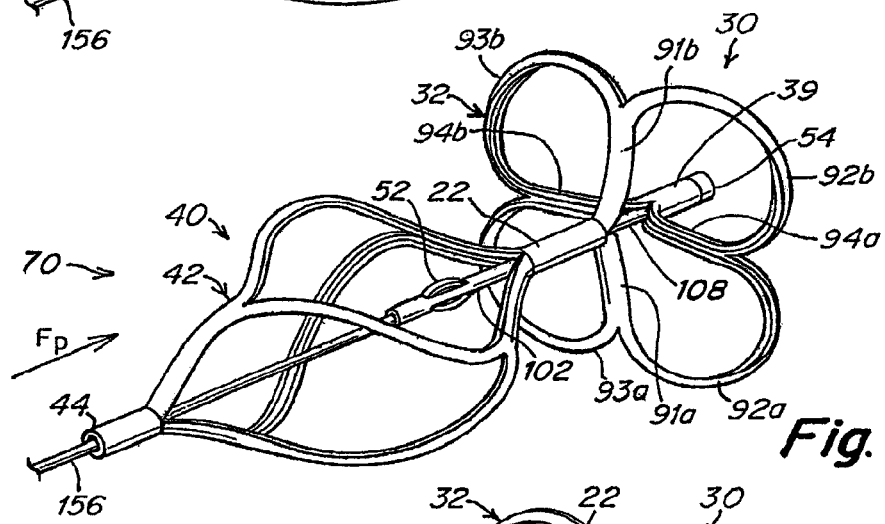
FIG. 4 illustrates an occluder and a catch member with the distal side of the occluder in its deployed configuration according to one embodiment of the invention.
Figure 5:
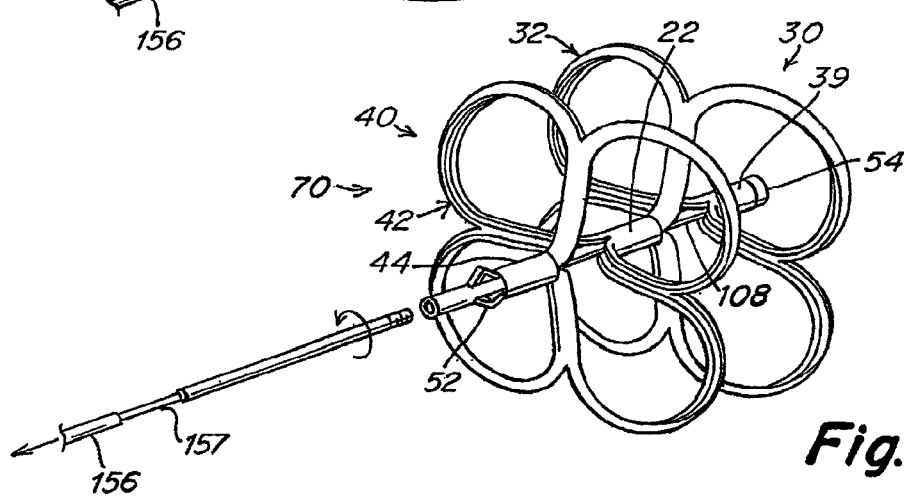
FIG. 5 illustrates an occluder and a catch member in a deployed configuration according to one embodiment of the invention.

FIGS. 2-5 illustrate an exemplary occluder with which systems and techniques disclosed herein may be used. A catch member 50 contains a proximal catch element 52 and a distal catch element, such as a flange 54, and is designed to be disposed at the distal end of tube 25 of occluder 70. Occluder 70, for example, can be formed by cutting a series of slits on tube 25. As shown in FIGS. 3-5, distal petals 32 are produced by cutting slits 31 in the upper portion of tube 25 according to the cutting pattern shown in FIG. 2. As shown in FIG. 3, the distal portion of the tube 25 is cut in half to form half sections 91a and 91b. The half sections 91a and 91b are further cut to a proximal distance from distal tip 39 into quarter sections 92a, 93a, 92b, and 93b. The cuts are discontinued and quarter sections 92a and 92b form half section 94a at distal tip 39, and quarter sections 93a and 93b form half section 94b at distal tip 39. Upon application of force $F_d$ to distal tip 39, struts defined by slits 31 bow and twist outward to form distal petals 32 in distal side 30, as shown in FIGS. 4-5. The movement of the struts during deployment is such that the struts rotate in an orthogonal plane relative to the axis of the device. Central tube 22 may be constrained during the application of force $F_d$, or any combination of forces sufficient to reduce the axial length of the tube 25 may be applied. One end of each of distal petals 32 originates from central tube 22, while the other end originates from distal tip 39 (FIGS. 3-4). Proximal petals 42 may be formed in proximal side 40, as shown in FIGS. 3-5, making slits 41 between central tube 22 and proximal tip 44, using the same cutting pattern described above.

The tube(s) 25 forming occluder 70 may be formed from a biocompatible metal or polymer. In at least some embodiments, occluder 70 is formed of a bioabsorbable polymer, or a shape memory polymer. Shape memory polymers can be advantageous so that the structure of the device assists in pressing the PFO tunnel closed. In other embodiments, occluder 70 is formed of a biocompatible metal, such as a shape memory alloy (e.g., nitinol). The thermal shape memory and/or superelastic properties of shape memory polymers and alloys permit occluder 70 to resume and maintain its intended shape in vivo despite being distorted during the delivery process. Alternatively, or additionally, occluder 70 may be formed of a bioabsorbable metal, such as iron, magnesium, or combinations of these and similar materials. Exemplary bioabsorbable polymers include polyhydroxyalkanoate compositions, for example poly-4-hydroxybutyrate (P4HB) compositions, disclosed in U.S. Pat. No. 6,610,764, entitled Polyhydroxyalkanoate Compositions Having Controlled Degradation Rate and U.S. Pat. No. 6,548,569, entitled Medical Devices and Applications of Polyhydroxyalkanoate Polymers, both of which are incorporated by reference in their entirety.

The cross-sectional shape of tube 25 may be circular or polygonal, for example square, or hexagonal. The slits 31 and 41 may be disposed on the face of the polygon (i.e., the flat part) or on the intersection of the faces.

The tube can be injection molded, extruded, or constructed of a sheet of material and rolled into a tube. The sheet of material could be a single ply sheet or multiple ply. The slits that form the struts could be cut or stamped into the sheet prior to rolling the sheet into a tube to connect the ends to form an enclosed cross section. Various geometrical cross sections are possible including circular, square, hexagonal and octagonal and the joint could be at the vertex or along the flat of a wall if the cross section is of a particular geometry. Various attachment techniques could be used to join the ends of the sheet to form a tube, including welding, heat adhesives, non-heat adhesives and other joining techniques suitable for in-vivo application.

The petal configuration is the deployed configuration. Occluder 70 can be secured in the petal configuration by a catch member that holds the ends of the tube 25 together, certain embodiments of which are described below. Use of the terms distal and proximal sides or portions 30 and 40, respectively, include the petals that are formed on the distal and proximal sides.

The embodiment described in conjunction with FIGS. 2-5 has similarities to the devices disclosed in U.S. patent application Ser. No. 10/890,784, entitled Tubular Patent Foramen Ovale (PFO) Closure Device with Locking Mechanism, filed on Jul. 14, 2004; U.S. patent application Ser. No. 11/070,027, entitled Delivery/Recovery System for Clover Leaf Septal Occluder, filed on Mar. 2, 2005; U.S. patent application Ser. No. 11/235,661, entitled Occluder Device Double Securement System for Delivery/Recovery of Such Occluder Device, filed Sep. 16, 2005; U.S. patent application Ser. No. 11/384,635, filed Mar. 20, 2006, entitled Catch Member for PFO Occluder; U.S. Patent Application No. 60/662,990, filed Mar. 18, 2004, entitled Suture Delivery/Recovery System for PFO Occluder with Catch System; and U.S. patent application Ser. No. 11/395,718, entitled Tubular Patent Foramen Ovale (PFO) Closure Device with Catch System, filed Mar. 31, 2006; all of which have the same assignee as the present application, and are incorporated by reference in their entirety. These incorporated documents describe how a device can be formed by making cuts or slits in a tube and compressing the ends, and how to deliver such a device. Embodiments of the catch members described herein are not restricted to the particular embodiment of occluder shown in FIGS. 2-5 and may be used with a number of devices and, in particular, may be used in conjunction with various devices described in the aforementioned patent applications.

In one alternate embodiment of an occluder, one end of each of distal petals originates from a central tube, while the other end originates from the distal end. Upon application of a force to the distal end to reduce the axial length, extended segments defined by slits in the tube bow and twist outward to form the distal petals in the distal side of the occluder. The movement of the segments during deployment is such that the segments rotate in an orthogonal plane relative to the axis of the device. The central tube may be constrained during the application of force, or any combination of forces sufficient to reduce the axial length of the tube may be applied. This embodiment is illustrated, for example, in FIGS. 2E-2H of U.S. patent application Ser. No. 11/395,718, which has been incorporated by reference above.

The transformable design of occluder 70 enables occluder 70 to be delivered in a low profile, tubular form and to be converted readily, i.e., by reducing the axial length, in place to the high-profile deployed configuration. Moreover, the conversion can readily be effected by forcing distal tip 39 and proximal tip 44 together. For example, distal side 30 and proximal side 40 of occluder 70 may be deployed in separate steps, or both distal side 30 and proximal side 40 of occluder 70 may be exposed (e.g., out of the delivery catheter) prior to engaging the catch member and deployed together as the catch member is engaged.

Occluder 70 may be prepared for delivery to an aperture 18a or 18b in any one of several ways. Slits 31 and 41 may be cut such that tube 25 bends into its intended configuration following deployment in vivo. Specifically, slits 31 and 41 may be cut to produce struts 32 and 42 of a thickness that facilitates the bending and formation of loops 32 and 42 upon the application of forces $F_d$ and/or $F_p$ during deployment. See FIGS. 3 and 4. Alternatively and/or additionally, a tube 25 formed of a shape memory material may be preformed into its intended configuration ex vivo so that it will recover its preformed shape once deployed in vivo. According to at least some embodiments, this preforming technique produces more reliable deployment and bending of occluder 70 in vivo. An intermediate approach may also be used: tube 25 may be only slightly preformed ex vivo such that it is predisposed to bend into its intended shape in vivo upon application of forces $F_d$ and $F_p$.

Figure 6:
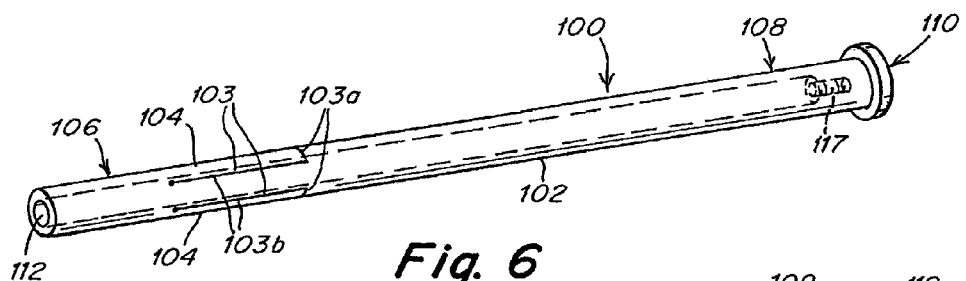
FIG. 6 is a view of cuts made during manufacture of a catch member according to one embodiment of the invention.
Figure 7:
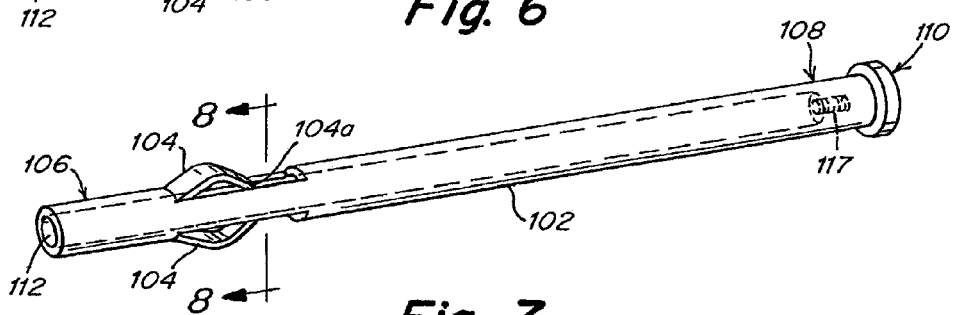
FIG. 7 is a view of a catch member according to one embodiment of the invention.
Figure 8:
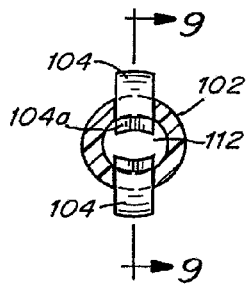
FIG. 8 is a cross-sectional view of the catch member along lines 8-8 in FIG. 7 according to one embodiment of the invention.
Figure 9:
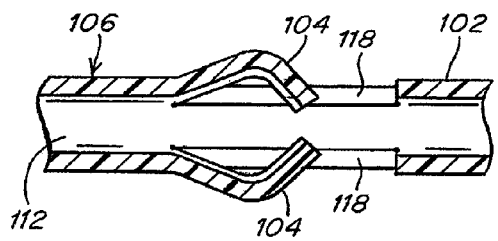
FIG. 9 is an exploded cross-sectional side view of the catch member along lines 9-9 in FIG. 8 according to one embodiment of the invention.

An embodiment of the catch member according to one aspect of the invention is illustrated in FIGS. 6-9. FIGS. 6 and 7 illustrate aspects of the manufacture of the catch member 100. Specifically, slits 103 (which include a transverse slit 103a and axial slits 103b) are cut into the proximal side 106 of the catch tube 102 to create arms 104, each arm having a distal surface 104a. Two arms 104 are illustrated. Of course, any number greater than one is possible. The geometrical constraints of the tube and manufacturing constraints of the slits would allow for up to 8 arms. Catch tube 102 is illustrated with a threaded portion 117, which is used to secure the delivery wire to the catch member, a central lumen 112 into which the delivery wire is adapted to go and a distal catch element 110 at the distal side 108 of the tube that serves to hold the distal end of the catch member to the occluder. The threaded portion 117 can be located at the proximal side 106 or the distal side 108 of the catch tube 102. By pushing arms 104 towards the proximal side 106 of the tube, arms 104 can be conditioned into a bent configuration as illustrated on FIG. 7. FIG. 8 illustrates the axial view of the arms 104 along lines 8-8 in FIG. 7. The conditioning process may include and can be enhanced by an annealing process, which can provide additional shape stability to the arms 104. After the conditioning process, arms 104 expand beyond the outside diameter of the catch tube 102. An expanded cross-sectional view of arms 104 in the bent configuration along lines 9-9 in FIG. 8 is shown in FIG. 9. FIG. 9 illustrates recess 118 created by the conditioning of arms 104 into the bent configuration. The arms can also be called "tabs", "stays", "holders", or any other suitable word or phrase. Referring to FIGS. 2-5, the distal side 108 of the catch tube may be ultrasonically welded to occluder 70, or some other fixing agent, such as glue, can be used. Also referring to FIGS. 2-5, the catch tube 102 is slidably disposed within the central tube 22 of occluder 70, and therefore, central tube 22 is able to slide against the catch tube 102 during the deployment and retrieval of occluder 70.

FIGS. 10 and 11 illustrate steps in the deployment of the catching mechanism according to one embodiment of the disclosure. Occluder 70 is introduced to an aperture 18*a* or 18*b* by a delivery sheath 154 in its delivery configuration. The delivery catheter 152 is positioned within the delivery sheath 154 with minimal clearance between them. The distal end of the delivery catheter 152 includes a threaded portion 153. In one embodiment, the threaded portion 153 is connected with the threaded portion 150 of the proximal tip 44 of the occluder. The distal tip 39 of the occluder is threadably connected to the delivery wire 156 at the threaded portion 117 of the catch tube 102. As shown in FIG. 10, the delivery wire has a recess 157, illustrated as a narrowing in the circumference, into which the arms 104 are rested, in unlocked position, during the delivery process. The recess 157 can vary in size and in some designs may be optional. As discussed above, the threaded portion 117 can be located at the proximal side 106 or at the distal side 108 of the catch tube 102.

Referring to FIG. 10, the distal side 30 of occluder 70 is exposed by withdrawing delivery sheath 152 proximally while holding delivery catheter 154 and delivery wire 156 stable. The distal side 30 of occluder 70 is deployed by advancing delivery catheter 154 distally to reduce the axial length between the central tube 22 and the distal tip 39 of occluder 70, while holding delivery sheath 152 and delivery wire 156 in place. Alternatively, the distal side 30 of occluder 70 is deployed by withdrawing delivery wire 156 proximally to reduce the axial length between the central tube 22 and the distal tip 39 of occluder 70, while holding delivery sheath 152 and delivery catheter 154 in place. Still referring to FIG. 10, the proximal side 40 of occluder 70 is exposed by further withdrawing delivery sheath 152 proximally while holding delivery catheter 154 and delivery wire 156 in place. The proximal side 40 of occluder 70 is deployed by advancing delivery catheter 154 distally to reduce the axial length between the central tube 22 and the proximal tip 44 of occluder 70, while holding delivery sheath 152 and delivery wire 156 in place. Alternatively, proximal side 40 of occluder 70 is deployed by withdrawing delivery wire 156 proximally to reduce the axial length between the central tube 22 and the proximal tip 44 of the occluder 70, while holding delivery sheath 152 and delivery catheter 154 in place. Referring to FIG. 11, occluder 70 is locked in its deployed configuration as the proximal tip 44 is advanced beyond arms 104. In this embodiment, arms 104 are partially activated, i.e. released into the temporary catch configuration illustrated in FIG. 11, when surface 156*a* of the delivery wire 156 collides with the distal surface 104*a* of arms 104. Occluder 70 is then released by unscrewing the threaded portion 153 of the delivery catheter 152 from the threaded portion 150, and unscrewing the threaded portion 117 of the catch tube 102 from the delivery wire 156. Withdrawal of delivery catheter 152 releases arms 104 into a permanent catch configuration illustrated in FIGS. 7-9.

FIG. 12A illustrates an alternative embodiment of the catch member after the delivery wire 156 has been unscrewed and withdrawn. In FIG. 12A, the embodiment of the proximal catch member has straight arms 180 with tips 182 exerting force against the proximal edge 151 of the threaded portion 150. As illustrated, the outer rim of the proximal edge touches tips 182.

FIG. 12B illustrates an alternative embodiment of the catch member after the delivery wire 156 has been unscrewed and withdrawn. In FIG. 12B, the embodiment of the proximal catch member has V-shaped arms 200 with tips 202 restraining movement of the proximal surface 151*a* of the proximal edge 151 of the occluder to prevent the occluder from expanding axially into its delivery configuration. While the embodiments of FIGS. 12A and 12B are illustrated with the threaded portion 117 at the distal side of arms 104, the threaded portion can also be located at the proximal side of arms 104.

FIG. 13 illustrates the initial step for a typical delivery sequence in accordance with one aspect of the disclosure. Occluder 224 and catch member 222 are secured to the delivery catheter 152 and to the delivery wire 156, respectively. The threaded portion of the delivery catheter 153 is screwed onto the male threaded portion 150 of occluder 224. The threaded portion of the delivery wire 156 is screwed onto the female threaded portion 117 of the catch member 222. Of course, the male and female threads can be reversed if desired. The distal end of the delivery sheath 154 with the enclosed occluder 224 is inserted through the aperture to be occluded, such as the anatomical aperture 18*a* or 18*b* of FIG. 1, to approximately the midpoint of the occluder 224.

Figure 15:
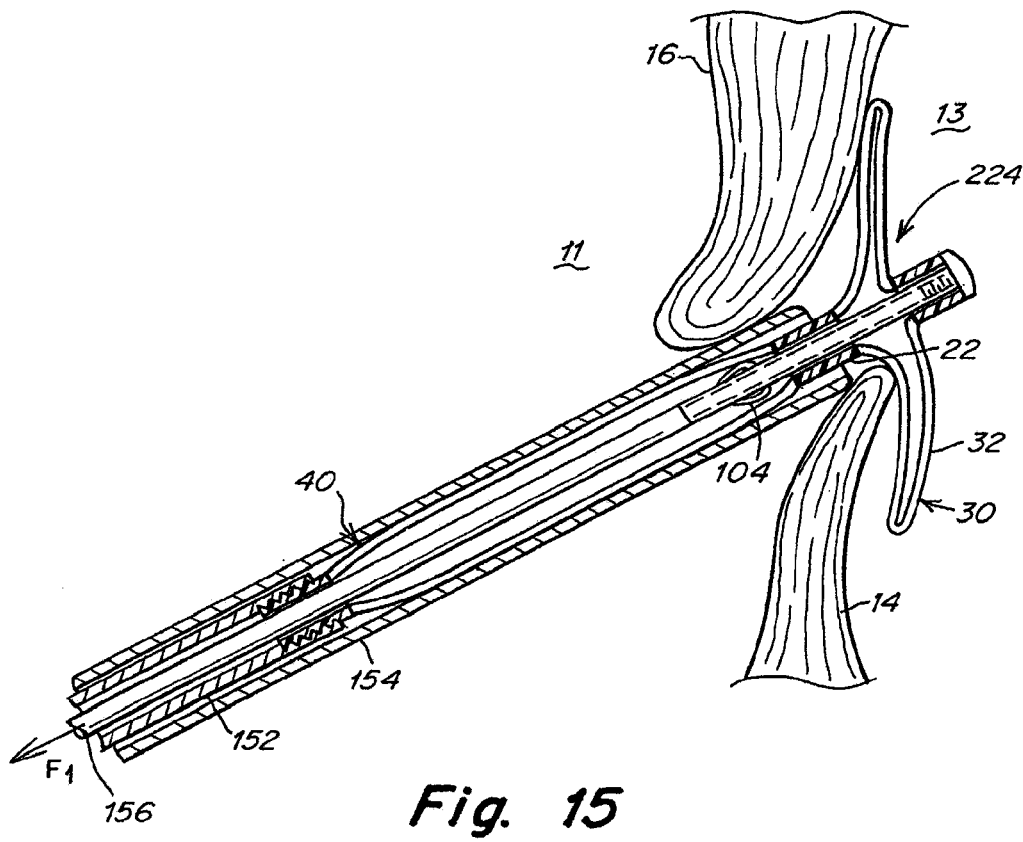

Referring now to FIG. 14, the distal side 30 of occluder 224 is deployed on the distal side of the aperture in the left atrium 13. The distal portion 30 is deployed by first retracting the delivery sheath 154 to expose the distal portion 30 of occluder 224. Force $F_2$ is simultaneously applied to the delivery catheter 152 and delivery wire 156 to hold occluder 224 stationary. Referring now to FIG. 15, the axial length of occluder 224 is then reduced by applying pulling force $F_1$ on the delivery wire 156 with sufficient force to cause arms 104 of the catch member 222 to be pulled through the central tube 22 of occluder 224 and the distal portion 30 of occluder 224 to compress and the distal petals 32 to form. The central tube 22 of occluder 224 catches on the catch member 222. This holds the distal petals 32 in place while the remainder of the deployment sequence is carried out.

Figure 16:
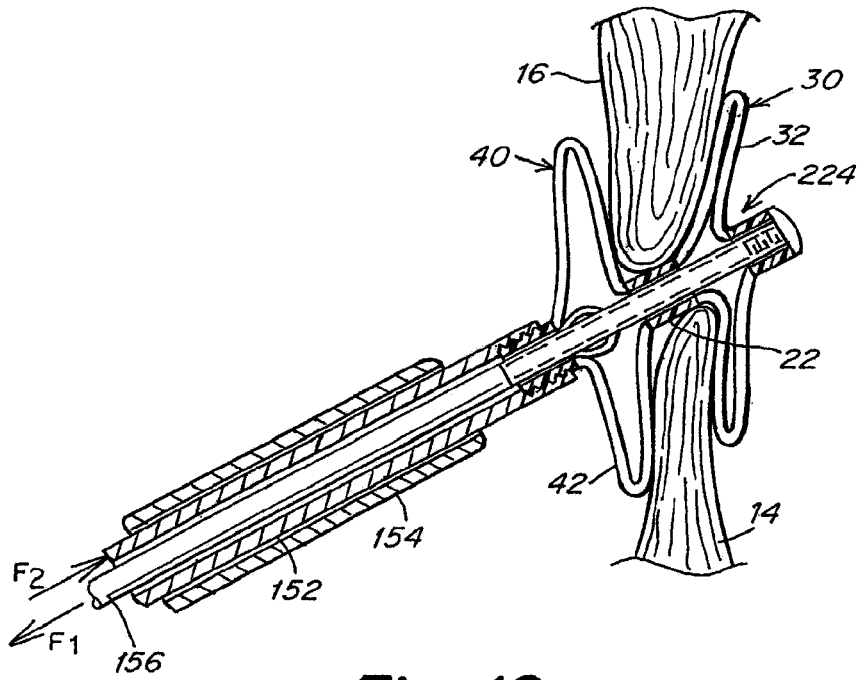
Figure 17:
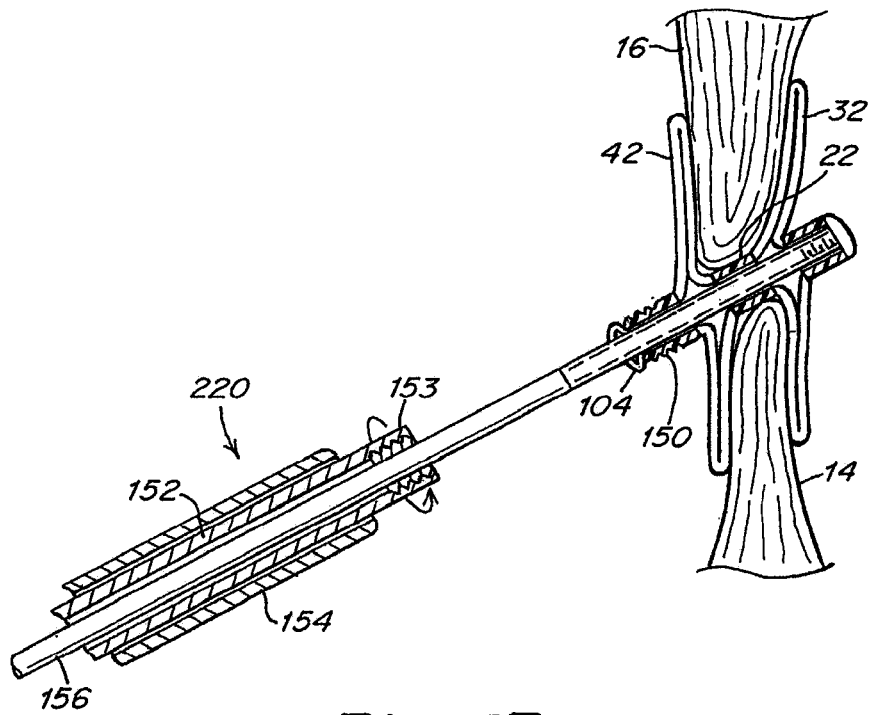

Referring now to FIG. 16, the proximal side 40 of occluder 224 is deployed on the proximal side of the aperture in the right atrium 11. The proximal portion 40 is deployed by first retracting the delivery sheath 154 to expose the proximal portion 40 of occluder 224. The proximal petals 42 are then formed by simultaneously advancing the delivery catheter 152 by applying force $F_2$ and retracting the delivery wire 156 by applying force $F_1$ to maintain the position of occluder 224. Eventually, the proximal tip 44 of occluder 224 is pushed over arms 104 of the catch member 222 and occluder 224 is caught on the distal surface 104*a* of arms 104. After the delivery catheter 152 is detached from occluder 224, the resulting configuration is illustrated in FIG. 17

Occluder 224 can now be evaluated for proper deployment at the desired location, for example by fluoroscopy or any other suitable technique with the delivery system 220, including delivery sheath 154, delivery catheter 152, and delivery wire 156 attached or partially detached. The delivery system 220 can be partially detached by releasing the securement system provided by the threaded connection to the proximal tip of the occluder. As shown in FIG. 17, according to one preferred embodiment, to evaluate the proper deployment of the occluder, if desired, the delivery sheath 154 can be further retracted and the delivery catheter 152 can be detached from occluder 224. The delivery catheter 152 can be detached by applying torque to unscrew the delivery catheter 152 from the proximal threaded portion 150 of occluder 224 and retracting the delivery catheter 152. The delivery wire 156 continues to secure occluder 224, as illustrated in FIG. 17. This affords the clinician a substantially unobstructed view of the occluder delivery site in order to evaluate the placement of occluder 224. In addition, the more flexible distal portions of the delivery catheter 152 and the delivery wire 156 allow the distal end of the delivery system 220 and the deployed occluder to be re-positioned so that the view is not obstructed. The positioning of occluder 224 can be evaluated using fluoroscopy or other appropriate techniques.

If the delivery or deployment is not satisfactory, while the delivery wire 156 continues to secure occluder 224, then the occluder can be retrieved or repositioned in the sequence shown in FIGS. 18-22.

Figure 18:
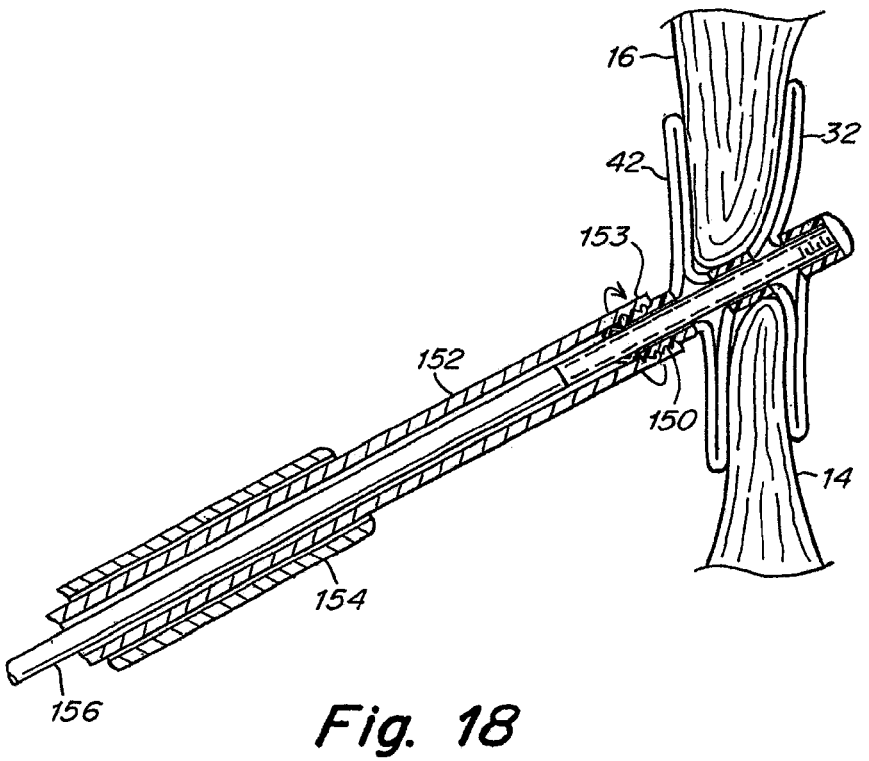

As illustrated in FIG. 18, if delivery catheter 152 has been detached, it is reattached by advancing the threaded portion 153 of the delivery catheter 152 toward the threaded portion 150 of occluder 224 and applying torque until the delivery catheter 152 is threaded onto the threaded portion 150 of occluder 224, as illustrated in FIG. 18.

Figure 19:
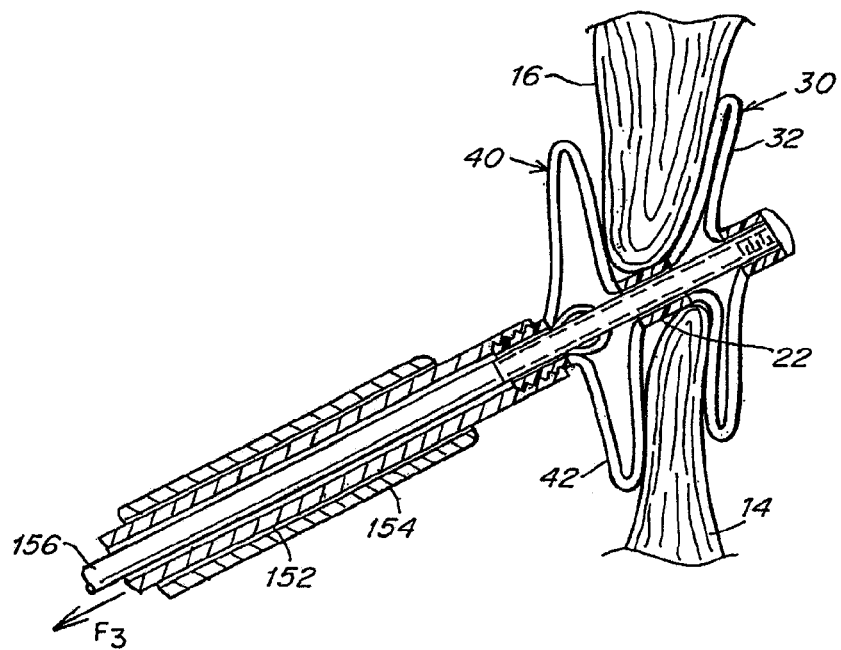
Figure 20:
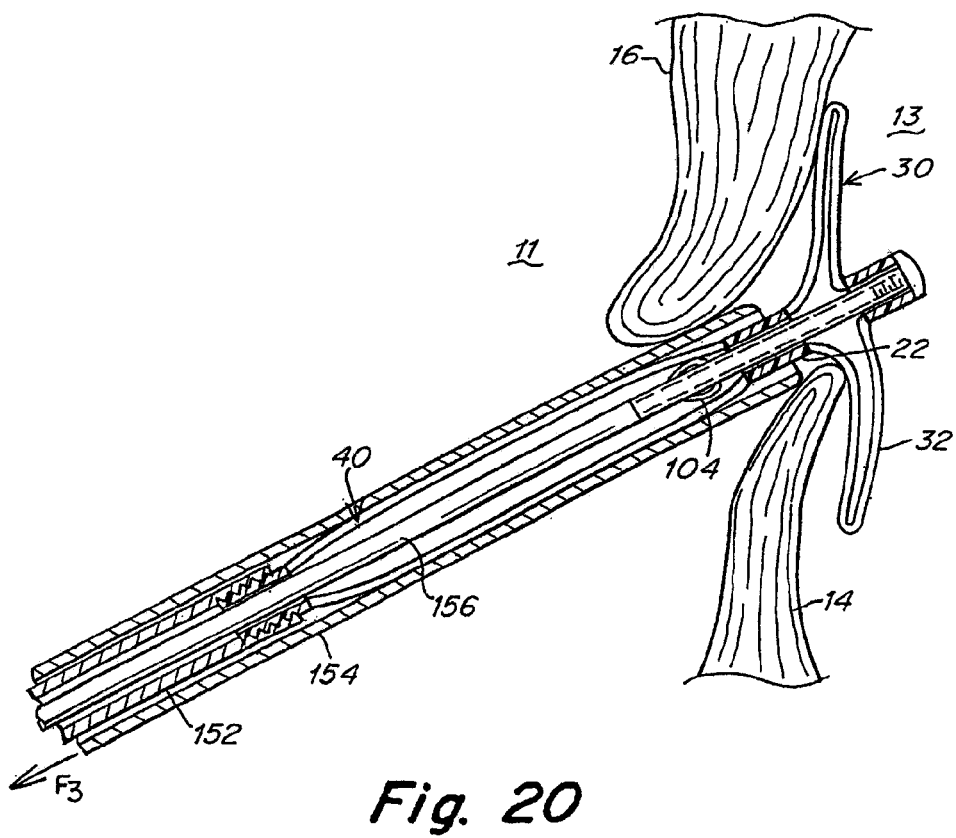

Referring now to FIG. 19, the delivery sheath 154 is pushed towards occluder 224. Then force $F_3$ is applied to the delivery catheter 152 to pull the proximal portion 40 of occluder 224 over the arms 104 of the catch member 222. Referring to FIG. 20, as the delivery sheath 154 is advanced distally to cover the proximal portion 40 of occluder 224, the axial length of occluder 224 is increased, the proximal petals 42 are unformed and the proximal portion 40 of occluder 224 returns to its tubular profile. Referring to FIG. 21, force $F_5$ is applied to the delivery sheath 154 to advance it over the proximal portion 40 of occluder 224 and retain the proximal portion 40 of occluder 224 in the low-profile configuration. Also, force $F_6$ is applied to the delivery wire 156 in order to release the distal portion 30 of occluder 224 and further increase the axial length of occluder 224.

Referring now to FIG. 22, the distal portion 30 of occluder 224 is fully extended back into its low-profile configuration and forces $F_7$ and $F_8$ are applied to the delivery sheath 154 and the delivery catheter 152 in order to retrieve occluder 224 back into delivery sheath 154.

Figure 23:
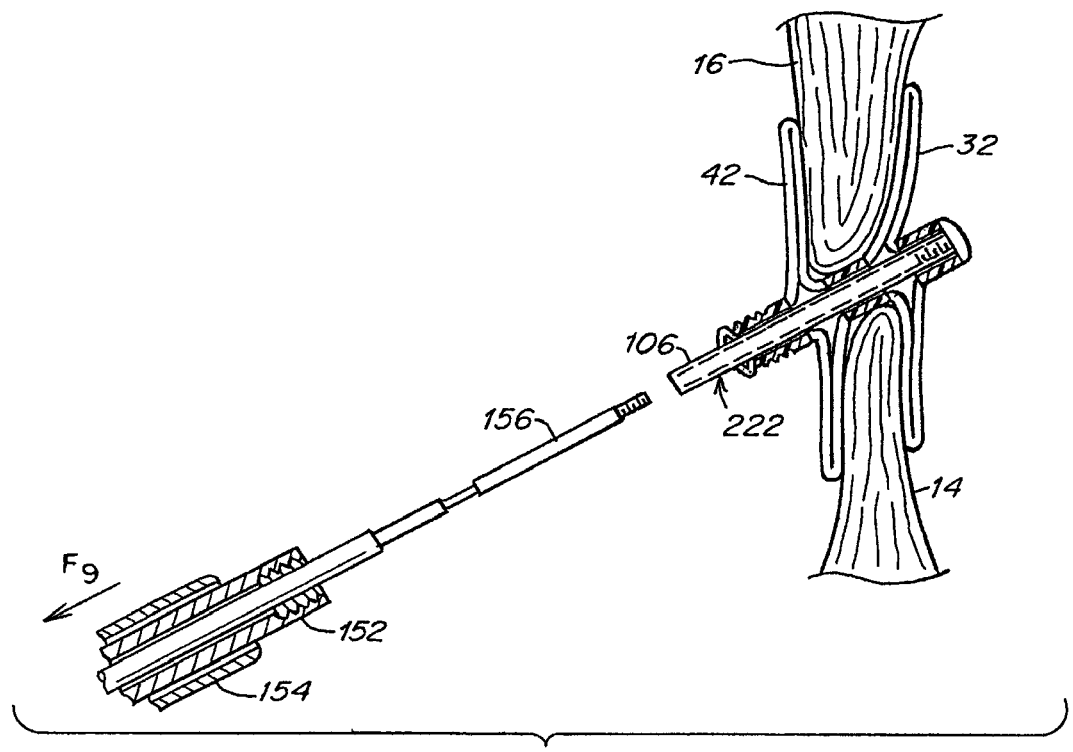
FIG. 23 is a cross-sectional side view of a detachment step according to one embodiment of the invention.

FIG. 23 illustrates the detachment of the delivery wire 156 from the catch member 222 when an occluder is fully deployed and its position is satisfactory. The threaded portion of the delivery wire 156 is unscrewed from the threaded portion 117 of the catch member and the delivery wire 156 is then retracted into the delivery catheter 152. The delivery wire 156, the delivery catheter 152 and the delivery sheath 154 are then removed from the heart 10 by application of force $F_9$.

Figure 24:
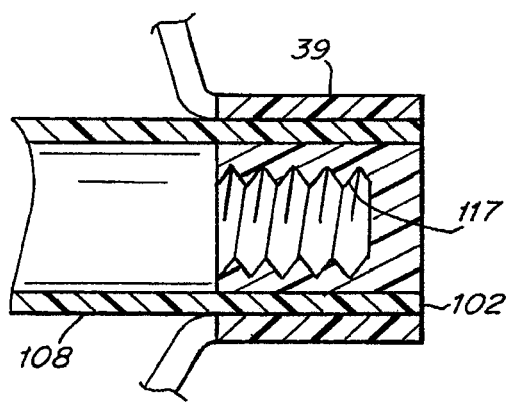
FIG. 24 is an exploded view of an embodiment of the distal portion of the catch member according to one aspect of the invention.

FIG. 24 illustrates an embodiment of the distal end of the catch member 222, in which the distal tip 39 of the occluder is welded to the catch tube 102 using ultrasonic energy, heat, adhesive, or a solvent. Alternatively, both the catch member 222 and the catch tube 102 can be made of one piece. The threaded portion 117 may be disposed anywhere along the axis of the catch tube. In a preferred form, the threaded portion 117 may be immediately distal to arms 104, not illustrated in FIG. 24.

Figure 25:
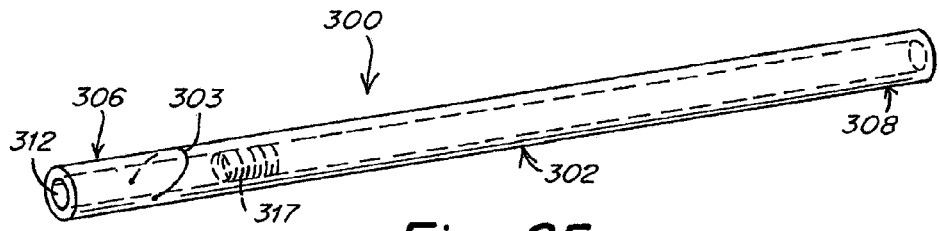
FIG. 25 is a view of the cut(s) made during the manufacture of a catch member according to one embodiment of the invention.
Figure 26:
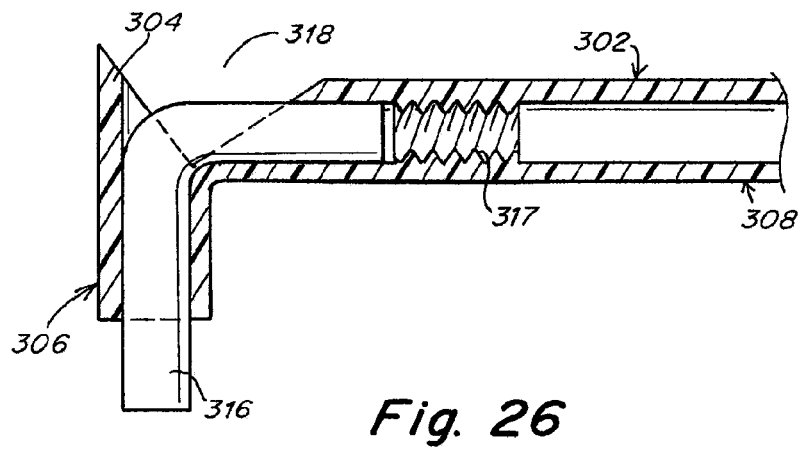
FIG. 26 is a cross-sectional view of a step in the manufacture of the catch member according to one embodiment of the invention.

Another embodiment of the catch member according to the disclosure is illustrated in FIGS. 25-28. FIGS. 25 and 26 illustrate exemplary steps in the manufacture of a catch member 300 by cutting a slit 303 into the proximal side 306 of the catch tube 302 to create a transverse, angled cut. The cut can be made at different angles with respect to the axis of the catch tube 302. In a preferred form, the cut can be at approximately 45 degrees. Catch tube 302 is illustrated with a central lumen 312 and a threaded portion 317 at the distal side 308 of the tube. The threaded portion 317 may be at any location on the catch tube. In one embodiment, a distal catch element is attached to the distal end 308 of the catch member via ultrasonic welding, heat welding, solvent bonding, or adhesive. In another embodiment, the distal side 308 of the catch tube 302 is directly attached to the distal end 39 of the occluder via ultrasonic welding, heat welding, solvent bonding, or adhesive as shown, for example, in FIG. 24.

Figure 27:
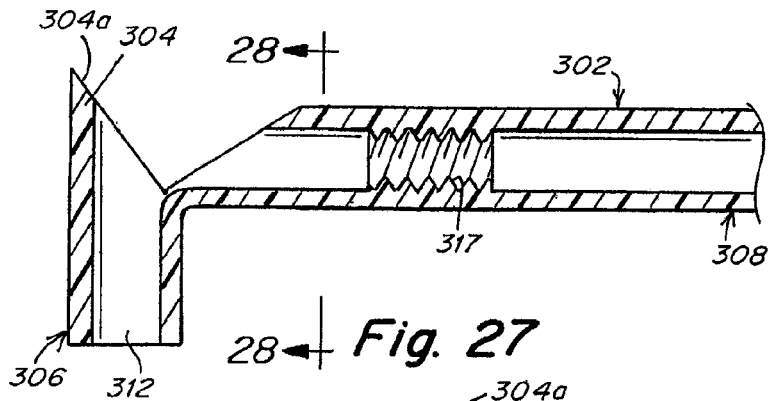
FIG. 27 is an exploded cross-sectional view of the catch member according to one embodiment of the invention.
Figure 28:
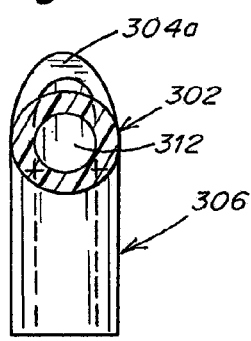
FIG. 28 is an exploded cross-sectional side view of the catch member along lines 28-28 in FIG. 27 according to one embodiment of the invention.

By conditioning the axis of the proximal side 306 to be at an angle, for example at a right angle, with respect to the axis of the distal side 308, the proximal side 306 can be conditioned into a bent configuration, for example by annealing. An example of a step in this process is illustrated on FIG. 26, where an annealing wire 316 is used to hold the proximal side 306 and the distal side 308 in a non-parallel configuration to create an opening 318. FIG. 27 illustrates an exploded cross-sectional view of the catch member 300 in a bent configuration. The axes of the proximal side 306 and distal side 308 of the catch tube 302 are shown at approximately a right angle, although smaller and larger angles are also encompassed by this disclosure. FIG. 28 illustrates a view of the proximal side 306 along lines 28-28 in FIG. 27, with the catching surface 304a of the catching tip 304a shown.

FIGS. 29 and 30 illustrate steps of the deployment sequence of the occluder according to one embodiment of the disclosure. Referring to FIG. 29, in one embodiment, the threaded portion 153 of the delivery catheter 152 is connected with the threaded portion 150 of the proximal tip 44 of the occluder. The distal tip 39 of the occluder is threadably connected to the delivery wire 156 at the threaded portion 317 of the catch tube 302. With the proximal side 306 and the distal side 308 of the catch tube 302 axially aligned and the delivery wire 156 held in place, delivery sheath 154 is withdrawn proximally to expose the distal side 30 of the occluder, delivery catheter 152 is pushed towards the distal tip 39 of the occluder to deploy the distal side 30. Referring now to FIG. 30, the proximal side 40 of the occluder is exposed by further withdrawing delivery sheath 154 proximally while holding delivery catheter 152 and delivery wire 156 in place. The proximal side 40 of the occluder is deployed by advancing delivery catheter 152 distally. Alternatively, proximal side 40 of the occluder is deployed by withdrawing delivery wire 156 proximally.

Referring to FIG. 31, upon full deployment of the occluder and upon satisfaction with its position, the occluder is released by unscrewing the delivery catheter 152 from the threaded portion 150 of the occluder, next unscrewing the delivery wire 156 from the threaded portion 317 of the catch tube 302, and finally withdrawing delivery catheter 152, delivery sheath 154, and delivery wire 156 proximally. Once the delivery wire 156 is unscrewed from the threaded portion 317 and withdrawn, the proximal side 306 of the catch tube 302 and the catching tip 304 are released into the bent configuration, which secures the occluder in the deployed configuration.

FIG. 31 illustrates a deployed occluder after the delivery wire 156 has been detached from the occluder. In this embodiment, surface 150a rests against the proximal side of the catch tube 306 and/or the catching surface 304a to maintain the occluder in a deployed configuration.

Another embodiment of a catch member according to the disclosure is illustrated in FIGS. 32-35. FIGS. 32 and 33 illustrate steps in the manufacture of the catch member 400 by cutting slits 403 into the proximal side 406 of the catch tube 402. Catch tube 402 is illustrated with a central lumen 412, a threaded portion 417, a stopper element 414 and a distal catch element 410. In one embodiment, the distal catch element 410 is attached to the distal end 39 of the occluder via ultrasonic welding, heat welding, solvent bonding, or adhesive as shown. In another embodiment, the distal side 408 of the catch tube 402 is directly attached to the distal end 39 of the occluder via ultrasonic welding, heat welding, solvent bonding, or adhesive as shown, for example, in FIG. 24. As illustrated in FIG. 33, the catch member 400 is conditioned to a deployed configuration by, for example, annealing with protrusions 404 formed. This can be done by applying forces $F_m$ to reduce the axial length of the catch tube 402 while annealing the catch tube 402, which results in formation of protrusions 404. While four protrusions are illustrated, more or fewer protrusions can be made and employed from the catch tube 402. In FIGS. 33-35, the catch member 400 is illustrated in a deployed configuration with protrusions 404 formed. In FIG. 32, the catch member 400 is in its delivery configuration with no protrusions formed as shown.

FIG. 34 illustrates a more detailed cross-sectional view of protrusions 404 and the stopper element 414. The stopper element 414 is firmly attached to the tube 402, and may contain one or more holes to connect the proximal lumen 412a to the distal lumen 412b. The stopper element is used to provide a stop for the delivery wire when being screwed in. FIG. 35 illustrates a view along lines 35-35 of FIG. 33. While the number of protrusions 404 illustrated in FIGS. 33-35 is four, a number greater or lesser than four is also encompassed by this disclosure.

FIGS. 36 and 37 illustrate steps of the deployment sequence of the occluder according to one embodiment of the disclosure. Referring to FIG. 36, the threaded portion 153 of the delivery catheter 152 is connected to the threaded portion 150 of the proximal tip 44 of the occluder. The distal tip 39 of the occluder is threadably connected to the delivery wire 156 at the threaded portion 417 of the catch tube 402. The catch member 400 is converted into a delivery configuration by screwing the delivery wire 156 into the threaded portion 417. As the delivery wire travels toward the distal side 408 of the catch tube 402, it hits the stopper element 414. Further screwing elongates protrusions 404 and converts the catch member 400 into its delivery configuration, as illustrated in FIGS. 36 and 37. Referring to FIG. 36, with the delivery wire 156 held in place, the delivery sheath 154 is withdrawn proximally to expose the distal side 30 of the occluder and the delivery catheter 152 is pushed towards the distal tip 39 of the occluder to deploy the distal side 30 of the occluder. Referring now to FIG. 37, the proximal side 40 of the occluder is exposed by further withdrawing the delivery sheath 154 proximally, while holding the delivery catheter 152 and the delivery wire 156 in place. The proximal side 40 of the occluder is deployed by advancing the delivery catheter 152 distally. Alternatively, the proximal side 40 of the occluder is deployed by withdrawing the delivery wire 156 proximally.

Referring to FIG. 38, upon full deployment of the occluder and satisfaction with its position, the occluder is released by unscrewing the delivery catheter 152 from the threaded portion 150 of the occluder, then unscrewing the delivery wire 156 from the threaded portion 417 of the catch tube 402, and finally withdrawing the delivery catheter 152, delivery sheath 154, and delivery wire 156 proximally. Once the delivery wire 156 is unscrewed from the threaded portion 417 and withdrawn, the catch member 400 is released into its deployed configuration with protrusions 404 formed.

The components of alternate embodiments of the catch member 400 described supra are described in connection with FIGS. 39-42.

Figure 39:
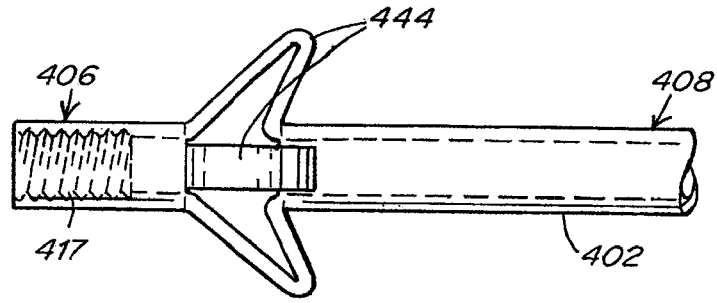
FIG. 39 is a view of a catch member according to one embodiment of the invention.
Figure 40:
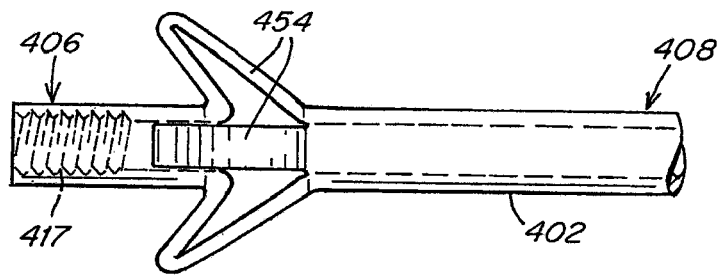
FIG. 40 is a view of a catch member according to one embodiment of the invention.

FIG. 39 illustrates the catch member 400 with protrusions 444 in the deployed configuration biased towards the distal side 408 of the catch tube 402. This biasing can be achieved by modification of the manufacturing process, a step of which is illustrated in FIG. 33. FIG. 40 illustrates the catch member 400 with protrusions 454 in the deployed configuration biased towards the proximal side 406 of the catch tube 402. This biasing can be achieved by modification of the manufacturing process, a step of which is illustrated in FIG. 33. In particular, annealing can be used to create alternate shapes.

Figure 41:
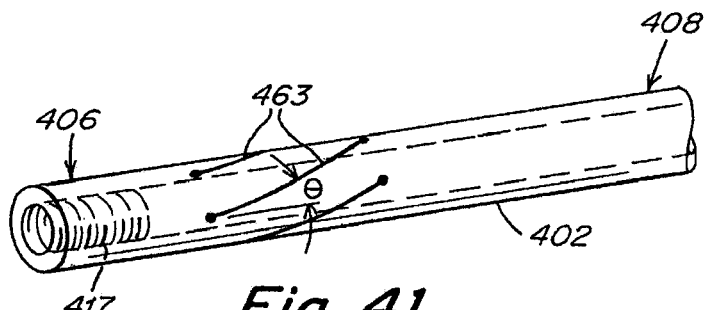
FIG. 41 is a view of cuts made during manufacture of a catch member according to one embodiment of the invention.
Figure 42:
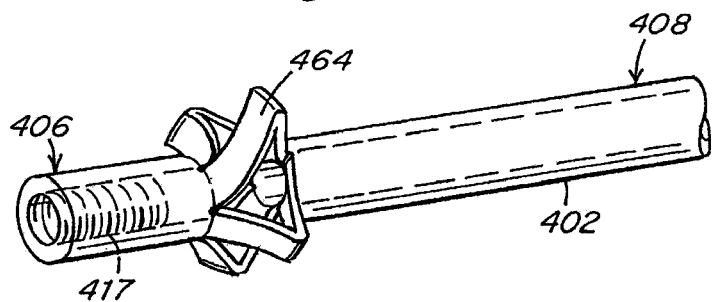
FIG. 42 is a view of a catch member according to one embodiment of the invention.

FIG. 41 illustrates yet another alternative embodiment of the catch member 400. In this embodiment, slits 463 are cut at an angle θ with respect to the axis of the catch tube 402. When forces are applied to compress the proximal side 406 and the distal side 408 of the catch tube 402, as illustrated for example in FIG. 33, the proximal side 406 will twist with respect to the distal side 408, which will result in protrusions 464 having a twisted shape as illustrated in FIG. 42.

Figure 43A:
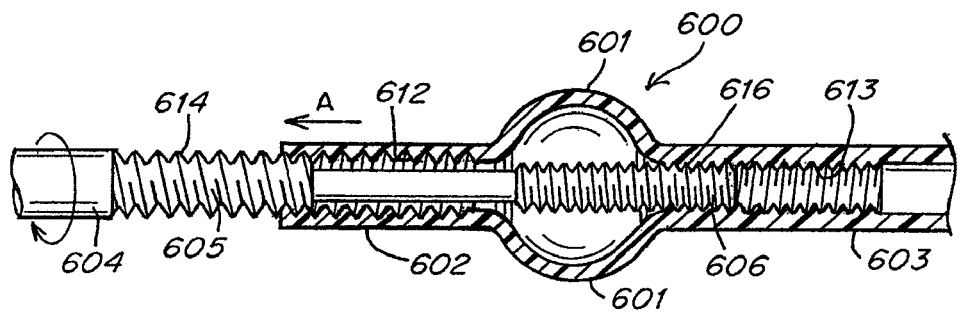
FIG. 43A illustrates an embodiment of the proximal catch element in a starting configuration according to one aspect of the invention.
Figure 43B:
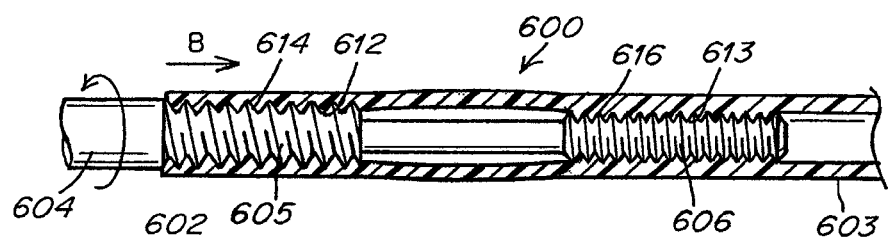
FIG. 43B illustrates an embodiment of the proximal catch element in a temporary catch configuration according to one aspect of the invention.
Figure 44:
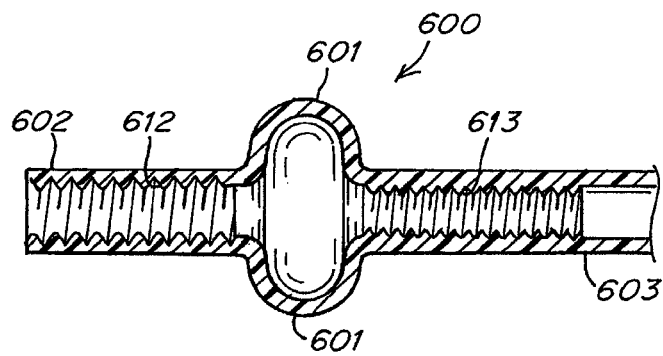
FIG. 44 illustrates an embodiment of the proximal catch element in a permanent catch configuration according to one aspect of the invention.

FIGS. 43A, 43B and 44 illustrate another embodiment of the invention. In this embodiment, a catch system 600 includes a temporary and a permanent catch that are achieved by a bump 601 on the proximal portion of a catch system, for example a catch tube by the use of two threads of different pitches. During manufacture of the catch system, bump 601 is formed on the proximal side of the tube by a material processing technique such as annealing. The use of two different pitches allows the catch member to be elongated in a delivery (reduced profile) configuration when a delivery wire is attached to the catch member. As the delivery wire is unscrewed from the catch member, the bump re-forms to provide a catch.

FIG. 43A illustrates a cross-section of the proximal portion of the catch member during the deployment stage. The proximal end of the catch member, proximal to bump 601, rests on the proximal section of the delivery wire 604. A proximal section 605 of the delivery wire 604 has a larger diameter than the distal section of the delivery wire 606. The difference in diameters can be smaller or larger than the difference illustrated in FIGS. 43A, 43B and 44. In one embodiment, diameters of the proximal section of the delivery wire 604 and the distal section of the delivery wire 606 may be nearly identical.

Still referring to FIG. 43A, a delivery wire has a smaller diameter at its distal section 606 and a larger diameter at its proximal section 604. The difference in diameters can be smaller or larger than the difference illustrated in FIGS. 43A, 43B, and 44. The proximal side of the delivery wire 604 has a thread 614 and the distal side of the delivery wire 606 has a thread 616. The proximal end 602 of the catch member 600 has a matching thread 612 to thread 614 of the same pitch. The distal end 603 of the catch member has a matching thread 613 to thread 616 of the same pitch. Thread 614 has a larger pitch than thread 616, by at least 0.01 of an inch.

During the occluder delivery process, the delivery wire 605 is advanced distally by threadably connecting threaded portion 613 of the delivery wire 605 and the threaded portion 616 of the catch member 600, and threaded portion 614 of the delivery wire 605 and the threaded portion 612 of the catch member 600. Because threaded portions 613 and 616 have a smaller pitch than threaded portions 612 and 614, this results in the proximal end 602 advancing in the direction, indicated by arrow A relative to the delivery wire 605, faster than the distal end 603. Bump 601 of the catch member 600 is therefore elongated, and the catch member 600 is reduced to its delivery profile. The resultant configuration is illustrated in FIG. 43B.

FIG. 43B illustrates the catch member in the delivery stage of the deployment process. In this delivery configuration, bump 601 is reduced to a lower-profile configuration, allowing for a device, such as an occluder, to slide more easily over bump 601. In this configuration, with the delivery wire 605 still attached, the catch member 600 could temporarily catch the occluder during its deployment with its proximal section of larger diameter. This may be useful during deployment, retrieval, repositioning or evaluation of deployment of an occluder. Once this is satisfactory, the delivery wire 605 can be removed by withdrawing it proximally. Removal of the delivery wire 605 results in the proximal end 602 moving in direction B faster than the distal end 603, creating the high-profile configuration of bump 601 as illustrated in FIG. 44. Generally, it may be desirable that this be accomplished in 1-10 turns, more preferably within 3-5 turns. Examples of suitable pitches include 0.011 inch pitch for threaded portion 613 of the catch member 600 and threaded portion 616 of the threaded wire 605, and 0.030 inch pitch for threaded portion 612 of the catch member 600 and threaded portion 614 of the threaded wire 605, or 0.011 inch pitch for threaded portion 613 of the catch member 600 and threaded portion 616 of the threaded wire 605, and 0.025 inch pitch for threaded portion 612 of the catch member 600 and threaded portion 614 of the threaded wire 605.

FIG. 44 illustrates the catch member once the delivery wire has been detached and removed, creating a permanent catch for the occluder at its deployed configuration. As a result of the pressure on bump 601, exerted by the proximal end of the occluder to be caught, proximal end 602 of the catch member 600 may constrict, for example at threads 612, and create a permanent catch. Alternatively, the material may provide sufficient stability to allow the bump to maintain the device in the delivered configuration.

Materials suitable for use with this embodiment include materials that are able to be easily deformed, for example metals, alloys, polymers, or combinations of these and similar materials. Examples include, but are not limited to, bioabsorbable polymers such as polyhroxyalkanoate compositions such as poly-4-hydroxybutyrate, bioabsorbable metals such as iron and magnesium.

Figure 45A:
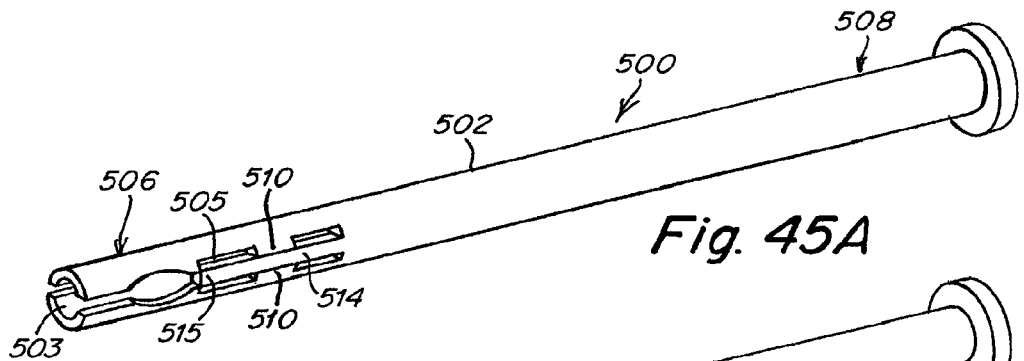
FIG. 45A illustrates a step in the manufacture of the catch member according to one embodiment of the invention.

FIG. 45A illustrates a step in the manufacture of the catch member according to one aspect of the disclosure. Catch tube 502 is illustrated with lumen 503, steps 510, tabs 514 and lumens 505, located at the proximal side 506 of the catch member. Tabs 514 and steps 510 can be made of the same piece of material as catch tube 502, or they can be separate pieces made from the same, or different material. The vertical spacing between steps 510 is equal or slightly larger than the height of tabs 514 to allow tabs 514 to slide between steps 510 without leaving more than a minimal clearance between steps 510 and tabs 514. Bump 504 (e.g. as shown in FIG. 45B) can be created, for example by compressing the proximal and distal ends 506 and 508, respectively, of the catch tube during annealing, similar to a scheme illustrated in FIG. 33.

Figure 45B:
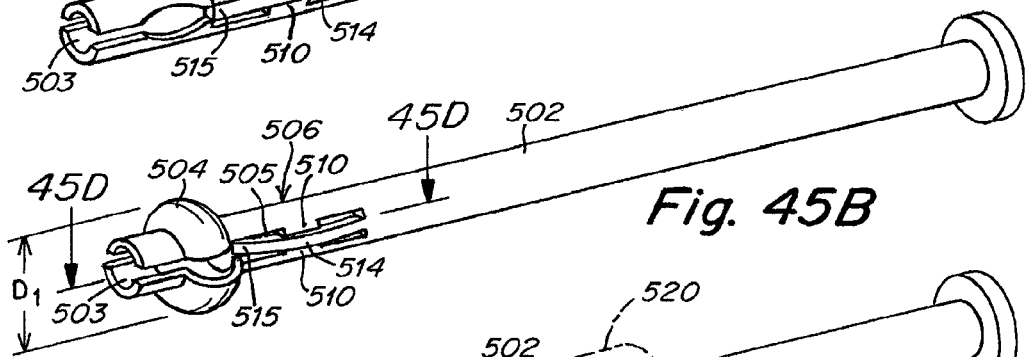
FIGS. 45B, 45D, 45F and 45H illustrate an embodiment of the catch member in a permanent catch configuration according to one aspect of the invention.
Figure 45C:
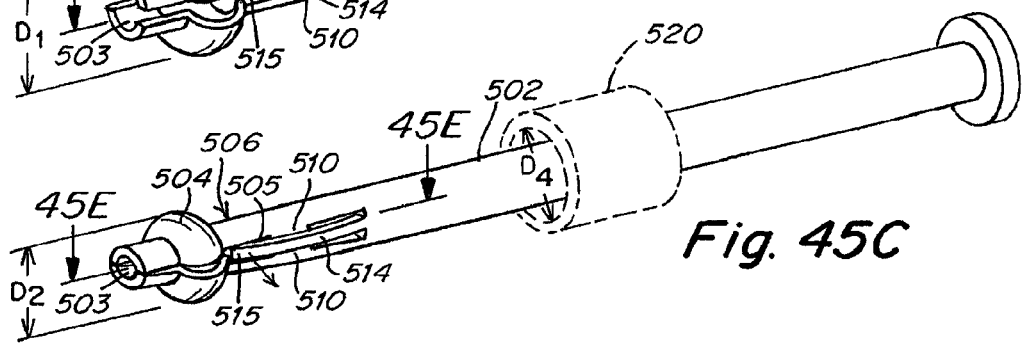
FIGS. 45C, 45E, 45G and 45I illustrate an embodiment of the catch member in a temporary catch configuration according to one aspect of the invention.
Figure 45D:
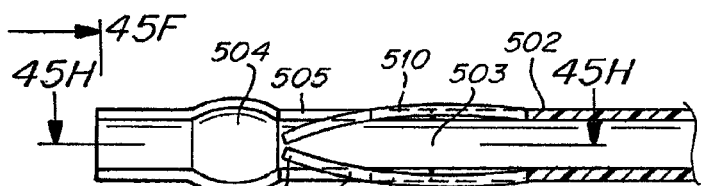

FIG. 45B illustrates an embodiment of the catch member in a permanent catch configuration. Bump 504 has an outside diameter $D_1$, which is larger than diameter of tube 502. Alternate bump configurations, including, but not limited to arms, barbs or other protrusions, are also encompassed by this disclosure. Tabs 514 are preformed, for example by annealing, into a curvilinear shape (although other suitable shapes also possible), such that when the catch member is not in contact with any other object (such as a delivery wire or an occluder), tabs 510 slide between steps 510 through lumen 505, so that tab tips 515 protrude into lumen 503. One function of tab tips 515 protruding into the lumen is to prevent the bump 504 from being compressed. This configuration can provide a permanent catch. This configuration is further illustrated in FIG. 45D, which is a view along lines 45D-45D in FIG. 45B. Another view of the same configuration is illustrated in FIG. 45F, which is a view along lines 45F-45F in FIG. 45D. FIG. 45H is a view along lines 45G-45G in FIG. 45D. FIG. 45H illustrates how tabs 514 prevent compression of the proximal side of the catch member 506 by sliding between steps 510. Therefore, application of pressure on bump 504 does not result in a substantively compressed configuration, also referred to as the temporary catch configuration, illustrated in FIGS. 45C, 45E, 45G and 45I.

A temporary catch configuration may be desired during deployment, retrieval, repositioning or evaluation of deployment of a device, such as an occluder. As illustrated in FIG. 45C, the proximal end of the catch member 506 can be compressed in a direction that reduces the volume of lumen 503. The vertical dimension of lumens 505 is larger than the height of tabs 514, to allow for compression of lumens 505 when tabs 514 (or tab tips 515) occupy lumens 505 as illustrated. This compressed configuration enables a device, or a portion of a device, such as a proximal portion of an occluder 520 with an inner diameter $D_4$, to reversibly slide over bump 504 by exerting enough force on bump 504 to compress the proximal side 506 of the catch member. In the compressed configuration, bump 504 has an outer diameter $D_2$, which is smaller than diameter $D_1$ (illustrated in FIG. 45B). A temporary catch configuration generally requires that the distal end of the delivery wire (not shown) occupies the distal portion of lumen 503.

Figure 45E:
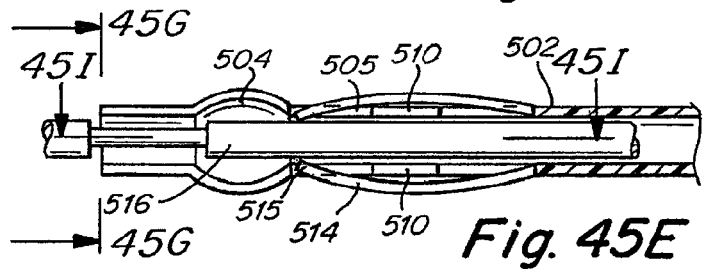
Figure 45F:
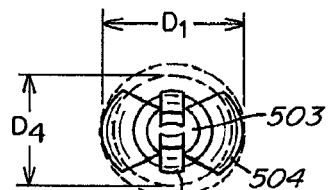
Figure 45G:
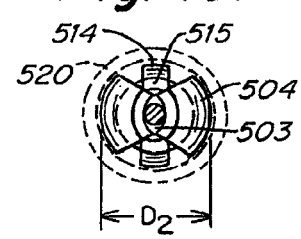
Figure 45H:
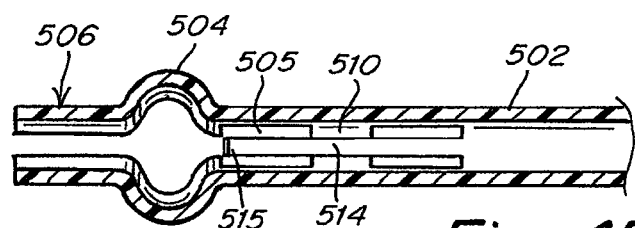
Figure 45I:
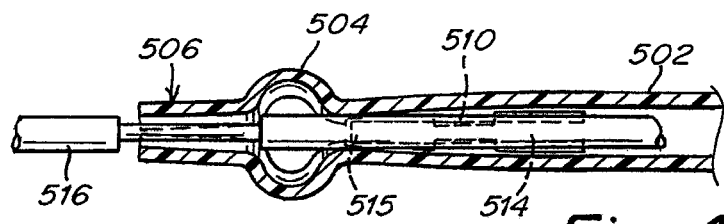

FIG. 45E is a view along lines 45E-45E in FIG. 45C, which further illustrates the temporary catch configuration. Delivery wire 516 is attached to the catch member and occupies a portion of lumen 503. Tab tips 515 rub against the delivery wire 516 and are pushed out of lumen 503 as illustrated. The curvilinear shape of tabs 514 results in tabs 514 curving around the outside of steps 510, allowing the proximal side of the catch member 506 to be compressed so that bump 504 has outside diameter $D_2$. This configuration is further illustrated in FIG. 45G, which is a view along lines 45G-45G in FIG. 45E. FIG. 45I illustrates how tabs 514 allow compression of the proximal side of the catch member 506 by being positioned outside of steps 510. Therefore application of pressure on bump 504 will result in a compressed configuration.

In embodiments of the invention, including the embodiments specifically illustrated and described herein, the catching configuration can be temporary or permanent. A temporary catch configuration generally allows for the catch member to release, while a permanent catch configuration generally is not designed for release. Certain embodiments have both a temporary catch configuration, which allows for confirmation of proper deployment, and a permanent catch configuration, that is engaged when proper deployment is confirmed. A permanent catch configuration can, for example, have a greater diameter at the proximal end of the catch member than a temporary catch configuration and may be engaged only after the device has been properly positioned. A temporary catch configuration is generally preferred during evaluation and repositioning of a device, such as an occluder, while a permanent catch configuration is generally preferred once the device is deployed.

The embodiments and techniques described here are described preferably for use with a device made of a polymer and formed from a single tube, such that the tube is a single monolithic material. The catch mechanism can be all or partly monolithic or integral with the tubular structure, or there can be an absence of any type of bonding or rigid connection to the rest of the tubular structure, in which case there may be some spring force or other force that holds the locking mechanism in place. While the device is thus shown as being substantially formed from a single tubular body, the catch mechanism as described in the embodiments above could be used with other types of devices, including those formed from many pieces, and including devices formed from other materials, including metals, polymers, stainless steel or nitinol.

The term "bioabsorbable," as used in the description above, is also understood to mean "bioresorbable."

While the description above refers to wires, and while the term "wire" might convey a more rigid piece than a string, a suture or a filament, all these terms are essentially interchangeable, and further include embodiments in which the wire, string, suture or filament is a hollow tube or conduit to allow another wire, as needed, to pass through its longitudinal axis. Each wire, string, suture and filament can be composed of one or more wires, strings, sutures and filaments.

In cases in which the device is made of a polymer, it can be desirable to add an additive or coating to the material to make it radiopaque to make it more visible in a wider variety of imaging techniques.

It will be appreciated that while a particular sequence of steps has been shown and described for purposes of explanation, the sequence may be varied in certain respects, or the steps may be combined, while still obtaining the desired deployment or in some cases to effect deployment in a particular way. For example, the delivery sheath may be advanced or retracted at varying times and in varying degrees, the proximal and distal portions of the occluder may be deployed into the petal configuration in a different sequence, etc. In addition, the steps could be automated.

The invention claimed is:

1. A collapsible medical device for occluding an aperture in a body, the medical device having a first configuration with a reduced profile and a second configuration with an expanded profile, the medical device being adapted to be delivered through a delivery system into a desired delivery location, the medical device comprising:

a proximal side and a distal side, disposed along a longitudinal axis;

an occluder portion movable between the first and second configurations; and, a catch system for holding the medical device in the second configuration including a generally tubular catch member having a central lumen disposed along the longitudinal axis with a proximal portion and a proximal end, the proximal portion having a raised portion around its outer circumference, tabs axially extending toward the raised portion along the longitudinal axis and terminating at distal tab tips, and a planar lumen intersecting the proximal end of the catch member, such that during deployment, the proximal end of the catch member is adapted to pass through an inner passageway of the occluder and to temporarily secure the device in an intermediate configuration by compression of the planar lumen and to secure the device in the second configuration when a proximal end of the device engages the raised portion, the engagement with the raised portion being secured by the tabs, wherein in the intermediate configuration the tab tips are disposed out of the central lumen, and wherein in the second configuration the tab tips are disposed in the central lumen.

2. The collapsible medical device of claim 1, wherein the device is a bioresorbable material.

* * * * *